United States Patent
Sawada et al.

(10) Patent No.: US 9,636,243 B2
(45) Date of Patent: May 2, 2017

(54) STENT DELIVERY SYSTEM

(71) Applicant: TERUMO KABUSHIKI KAISHA, Shibuya-ku (JP)

(72) Inventors: Satoshi Sawada, Shizuoka (JP); Naoto Nozawa, Shizuoka (JP); Takao Anzai, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 627 days.

(21) Appl. No.: 13/944,322

(22) Filed: Jul. 17, 2013

(65) Prior Publication Data

US 2013/0304183 A1    Nov. 14, 2013

Related U.S. Application Data

(63) Continuation of application No. PCT/JP2011/080474, filed on Dec. 28, 2011.

(30) Foreign Application Priority Data

Feb. 15, 2011   (JP) .................................. 2011-030149
Sep. 9, 2011    (JP) .................................. 2011-197417

(51) Int. Cl.
*A61F 2/958*     (2013.01)
*A61F 2/91*      (2013.01)
(Continued)

(52) U.S. Cl.
CPC ................ *A61F 2/958* (2013.01); *A61F 2/91* (2013.01); *A61F 2/915* (2013.01); *A61L 31/16* (2013.01);
(Continued)

(58) Field of Classification Search
CPC .. A61F 2/958; A61F 2/91; A61F 2/915; A61F 2230/0054; A61F 2210/0076;
(Continued)

(56) References Cited

U.S. PATENT DOCUMENTS 5,922,021 A * 7/1999 Jang .......................... A61F 2/91
                                                        623/1.15
8,455,094 B2    6/2013 Omata et al.
(Continued)

FOREIGN PATENT DOCUMENTS

JP    2003-062078 A    3/2003
JP    2005-520639 A    7/2005
(Continued)

OTHER PUBLICATIONS

Office Action issued on Aug. 18, 2015, by the Japan Patent Office in corresponding Japanese Patent Application No. 2012-557800, and an English Translation of the Office Action. (11 pages).
(Continued)

*Primary Examiner* — Kathleen Holwerda
(74) *Attorney, Agent, or Firm* — Buchanan Ingersoll & Rooney PC

(57) ABSTRACT

To provide a stent delivery system that can limit/prevent drop-off or shifting of a stent from the balloon. A stent delivery system that is equipped with a main tube-shaped shaft, a balloon provided on the tip of the main shaft, and a stent fitted so as to encircle the balloon, wherein a layer for preventing stent drop-off containing a compound with multiple thiol groups is formed on at least a portion of the balloon surface, and at least the portion of the stent that contacts the stent drop-off preventing layer is made of metal.

15 Claims, 5 Drawing Sheets

(51) Int. Cl.
*A61F 2/915* (2013.01)
*A61L 31/16* (2006.01)

(52) U.S. Cl.
CPC ............... *A61F 2002/91566* (2013.01); *A61F 2210/0076* (2013.01); *A61F 2230/0013* (2013.01); *A61F 2230/0054* (2013.01); *A61F 2250/0067* (2013.01); *A61L 2300/406* (2013.01); *A61L 2300/41* (2013.01); *A61L 2300/416* (2013.01)

(58) Field of Classification Search
CPC ...... A61F 2230/0013; A61F 2250/0067; A61F 2002/91566; A61L 31/16; A61L 2300/416; A61L 2300/406; A61L 2300/41; A61L 29/00–29/14; A61L 31/00–33/00
See application file for complete search history.

(56) References Cited

U.S. PATENT DOCUMENTS

| | | | |
|---|---|---|---|
| 2003/0004564 A1* | 1/2003 | Elkins | A61F 2/91 623/1.15 |
| 2003/0180488 A1 | 9/2003 | Lim et al. | |
| 2008/0287984 A1* | 11/2008 | Weber | A61L 29/126 606/194 |
| 2009/0054448 A1* | 2/2009 | Jones | C07C 323/60 514/252.12 |
| 2010/0121425 A1 | 5/2010 | Shimada | |
| 2011/0143014 A1* | 6/2011 | Stankus | A61F 2/958 427/2.14 |
| 2011/0274918 A1 | 11/2011 | Omata et al. | |

FOREIGN PATENT DOCUMENTS

| | | |
|---|---|---|
| JP | 2006-130064 A | 5/2006 |
| JP | 2007-097706 A | 4/2007 |
| JP | 2007-135880 A | 6/2007 |
| JP | 2008-284019 A | 11/2008 |
| JP | 2010-527700 A | 8/2010 |
| WO | WO 2008/126737 A1 | 10/2008 |
| WO | WO 2010/087286 A1 | 8/2010 |
| WO | WO 2010/087375 A1 | 8/2010 |

OTHER PUBLICATIONS

International Search Report (PCT/ISA/210) issued on Feb. 7, 2012, by the Japanese Patent Office as the International Searching Authority for International Application No. PCT/JP2011/080474.

* cited by examiner

STENT DELIVERY SYSTEM

This application is a continuation of International Application No. PCT/JP2011/080474 filed on Dec. 28, 2011, and claims priority to Japanese Patent Application No. 2011-30149 filed on Feb. 15, 2011 and Japanese Patent Application No. 2011-197417 filed on Sep. 9, 2011, the entire content of each of which is incorporated herein by reference.

TECHNICAL FIELD

The present invention generally relates to a stent delivery system. More specifically, the present invention relates to a stent delivery system for use in improvement of a stenosed part formed in a living body lumen such as blood vessel, bile duct, trachea, esophagus, urethra, and other organs. Particularly, the present invention involves a stent delivery system by which a stent to be put indwelling in a stenosed lesion generated in a blood vessel, especially a coronary artery, can be delivered to the lesion safely and smoothly.

BACKGROUND DISCUSSION

A stent placement procedure has been practiced in which a stent is put indwelling (indwelled) in a stenosed part in a living body lumen such as blood vessel, bile duct, trachea, esophagus, urethra, and other organs so as to secure the lumen. The stents for use in the stent placement procedure are classified, according to the function and placement method, into balloon-expandable stents and self-expandable stents.

Of these stents, the self-expandable stents are ordinarily formed from a shape memory alloy or the like, and can expand without any mechanical stent-expanding operation. On the other hand, the balloon-expandable stents themselves do not have an expanding function. In order to put a balloon-expandable stent indwelling in a desired stenosed part, therefore, the following procedure is carried out, for example. The stent mounted to a balloon part of a balloon catheter is disposed in the desired stenosed part, thereafter the balloon is inflated, and the stent is expanded (plastically deformed) by the expansive force of the balloon, whereby the stent is brought into close contact with the inside surface of the stenosed part and fixed in situ. In the case of placement of a balloon-expandable stent, therefore, the balloon catheter has to be inserted to the stenosed part, with the stent mounted and fixed to the balloon part. Even if the stent is securely fixed to the balloon part, however, the load arising from friction between the stent and the blood vessel or the like may cause the stent to shift on the balloon during the inserting operation. Thus, there is a risk that the stent may drop off the balloon catheter or may be disposed in a position different from the desired stenosed part.

In addition, the balloon normally used for a balloon catheter has a shape in which truncated cone-shaped tapered sections are formed on the distal and proximal sides of a straight tube section which is expanded into a hollow cylindrical shape. The balloon-expandable stent is mounted onto the outside surface of the straight tube section. At the time of insertion into the stenosed part, the stent may shift on the balloon. Therefore, there are some cases in which, although the stent does not fall off the balloon catheter, the stent shifts distally or proximally on the straight tube section so that one end portion of the stent is located on the outside surface of the tapered section of the balloon. In such a situation, the stent portion located on the tapered section is expanded only into a shape according to the expansion of the tapered section. Consequently, the stent is expanded insufficiently, which may lead to restenosis.

In order to solve such a problem, a stent delivery system has been proposed in which a part of a balloon in a folded state is clamped between stent struts so as to form a secondary projected portion, whereby the stent is fixed to the balloon. An example of this stent delivery system is disclosed in Japanese Application Publication No. 2007-135880. In this disclosed system, a stent is disposed on a balloon of a balloon catheter, the stent is diametrically contracted (crimped), and thereafter a projected portion formed by inflating the balloon is clamped between the stent struts, whereby the stent is fixed to the balloon (see FIG. 2 and paragraphs [0025], [0028], and [0029] of Japanese Application Publication No. 2007-135880).

However, in the stent delivery system disclosed in the above-mentioned application publication, it is necessary to inflate the balloon after the stent is diametrically contracted (crimped), which complicates the manufacturing process. In addition, a stress is always imposed on the balloon portion (secondary projected portion) clamped between the stent struts, so that the strength of this portion is lowered with the lapse of time. This may result in cracking of the balloon or generation of a pinhole in the balloon when the stent is expanded.

SUMMARY

The stent delivery system disclosed here is configured so that drop-off of a stent from a balloon, or shifting of the stent on the balloon, is restrained or prevented during an inserting operation.

The stent delivery system is also able to restrain or prevent cracking of a balloon or generation of a pinhole in the balloon when the stent is expanded.

According to one aspect, a stent delivery system comprises: a tube-shaped shaft body; a balloon provided at a distal portion of the shaft body, the balloon possessing an outer surface; a stent drop-off preventing layer on at least a portion of the outer surface of the balloon to prevent drop-off of the stent from the balloon, with the stent drop-off preventing layer containing a compound with a plurality of thiol groups; a stent encircling the balloon and contacting the stent drop-off preventing layer; and at least a portion of the stent which makes contact with the stent drop-off preventing layer being made of a metal.

According to another aspect, a stent delivery system comprises: an inner tube positioned inside an outer tube, with the outer tube possessing a distal end and an inner surface, the inner tube possessing an outer surface and a distal end extending distally beyond the distal end of the outer tube, and a balloon inflation lumen located between the inner surface of the outer tube and the outer surface of the inner tube; and a balloon possessing a distal end fixed to a distal end portion of the inner tube and a proximal end fixed to a distal end of the outer tube. The balloon possesses an outer surface and an interior communicating with the balloon inflation lumen located between the inner surface of the outer tube and the outer surface of the inner tube. A hollow cylindrically shaped stent possesses open opposite ends, and also possesses an inner surface and an outer surface that communicate with one another by way of a plurality of cutouts provided in the hollow cylindrically shaped stent. The stent is expandable and contractable in a radial direction of the hollow cylindrically shaped stent, and at least a part of the stent is made of metal, with the balloon being positioned inside the hollow cylindrically shaped stent so that the hollow cylindrically shaped stent encircles the balloon. A layer containing a compound with a plurality of thiol groups is positioned between the outer surface of the balloon and the hollow cylindrically shaped stent, with at least a portion of the metal part of the hollow cylindrically shaped stent being bonded to the layer.

The compound with the thiol groups can be supported on the balloon surface by irradiation with an ionized gas plasma.

The compound with the thiol groups is at least one selected from the group consisting of 1,2-ethanedithiol, 1,2-propanedithiol, 1,3-propanedithiol, 1,4-butanedithiol, 2,3-butanedithiol, 1,5-pentanedithiol, 1,6-hexanedithiol, 1,8-octanedithiol, 3,6-dioxa-1,8-octanedithiol, bis(2-mercaptoethyl)ether, bis(2-mercaptoethyl) sulfide, 1,2-benzenedithiol, 1,4-benzenedithiol, 1,4-bis(mercaptomethyl)benzene, toluene-3,4-dithiol, 1,5-dimercaptonaphthalene, 4,4'-biphenyldithiol, 4,4'-thiobisbenzenethiol, tetraethylene glycol bis(3-mercaptopropionate), 1,3,5-benzenetrithiol, tris[(3-mercaptopropionyloxy)ethyl]isocyanurate (TEMPIC), triazinetrithiol, trimethylolpropane tris(3-mercaptopropionate) (TMMP), pentaerythritol tetrakis(mercaptoacetate), pentaerythritol tetrakis(3-mercaptopropionate) (PEMP), pentaerythritol tetrakis(3-mercaptobutyrate), dipentaerythritol hexakis(3-mercaptopropionate), and their derivatives and polymers.

A drug coat layer can be provided on a portion of the stent, on the side opposite to the portion making contact with the stent drop-off preventing layer.

The configuration of the stent delivery system disclosed here restrains or prevents drop-off of the stent from the balloon or shifting of the stent on the balloon by an interaction between the metallic portion of the stent and the stent drop-off preventing layer containing the compound with a plurality of thiol groups.

Another aspect involves a method comprising: applying a layer containing a compound with a plurality of thiol groups to an outer surface of an inflatable balloon; mounting a hollow stent on the balloon after applying the layer to the balloon so that the balloon is positioned inside the hollow stent, the hollow stent possessing open opposite ends, the stent also possessing an inner surface and an outer surface that communicate with one another by way of a plurality of cutouts provided in the hollow stent, at least a part of the stent being made of metal; and bonding at least a portion of the metal part of the stent to the layer on the balloon to prevent the stent from coming off the balloon when the stent mounted on the balloon is inserted into a living body lumen.

DETAILED DESCRIPTION

Figure 1:
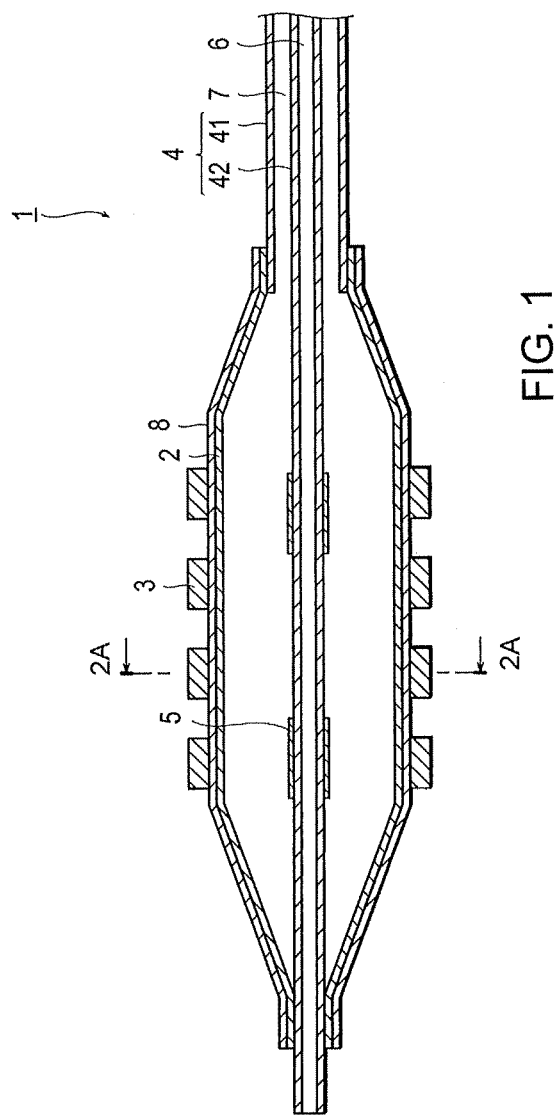
FIG. 1 is a longitudinal cross-sectional view, in an enlarged form, of a distal portion of one embodiment of the stent delivery system disclosed here (when a balloon is inflated).

Disclosed here and described in detail below is a stent delivery system including a tube-shaped shaft body, a balloon provided at a distal portion of the shaft body, and a stent so mounted as to encircle the balloon, wherein a layer for preventing stent drop-off (herein also referred to simply as "stent drop-off preventing layer") containing a compound with a plurality of thiol groups (herein also referred to simply as "thiol compound") is formed on at least a portion of a surface of the balloon, and at least that portion of the stent which makes contact with the stent drop-off preventing layer is made of a metal.

Conventionally, a balloon-expandable stent is passed through a stenosed part in use, thereby a strong load due to friction may be exerted on the stent. When it is intended to insert such a stent into a stenosed part in a living body lumen such as a blood vessel, bile duct, trachea, esophagus, urethra, and other organs, therefore, the strong load due to friction may cause the stent to shift to an undesired portion of the balloon (for example, to a tapered portion of the balloon) or in some cases to drop or fall off from the balloon (and further to drop or fall off from a catheter). The conventional stent delivery system having a stent crimped on a balloon is unsatisfactory for enduring the load. Thus, there has been a need for a stent delivery system of a structure that can endure stronger loads.

The stent delivery system disclosed here includes a layer containing a compound having a plurality of thiol groups (stent drop-off preventing layer) provided on a balloon surface that makes contact with a metallic portion of the stent. The stent drop-off preventing layer thus provided on the balloon surface restrains or prevents the stent from shifting. Therefore, even when the stent is inserted into a stenosed part in a living body lumen such as blood vessel, bile duct, trachea, esophagus, urethra, and other organs in the state of being crimped (diametrically contracted) on the balloon, shifting or drop-off of the stent from the balloon is not so likely to occur or will not occur at all. The reason the stent drop-off preventing layer restrains or prevents shifting of the stent has not been fully elucidated or determined, but is surmised as follows. The present invention is not to be restricted by the following surmise. The thiol groups (—SH groups; referred to also as mercapto groups, sulfhydryl groups, or hydrosulfide groups) or disulfide groups (—S—S— groups) derived from the thiol compound in the stent drop-off preventing layer and the metallic portion of the stent are bonded to each other by an interaction. Therefore, the use of the stent delivery system according to the disclosure here helps ensure that even if a strong load due to friction is exerted on the stent when the stent is inserted into a stenosed part in a living body lumen such as blood vessel, bile duct, trachea, esophagus, urethra, and other organs in the state of being crimpled (diametrically contracted) on a balloon, the stent can sufficiently endure the load, and the stent is effectively restrained or prevented from dropping off from, or shifting on, the balloon.

In addition, as above-mentioned, in the stent delivery system disclosed here, its effect (particularly, the effect of restraining or preventing drop-off or shifting of the stent) can be sufficiently exhibited even in a state where the stent is only crimped (diametrically contracted) on the balloon. In other words, unlike in the case of the above-mentioned Japanese patent application publication, it is unnecessary to clamp a portion of the folded balloon between stent struts after the stent is crimped (diametrically contracted). Consequently, cracking of the balloon or generation of a pinhole in the balloon can be restrained or prevented from occurring when the stent is expanded.

As above-mentioned, the stent delivery system disclosed here can exhibit its effect especially when applied to a balloon-expandable stent.

The stent delivery system disclosed here includes the stent drop-off preventing layer containing a compound with a plurality of thiol groups, with such layer being formed on a balloon surface that makes contact with a metallic stent. Therefore, parts other than the balloon part of the stent delivery system can be applied in the same manner as (i.e., can be configured in the same way as), or through an appropriate modification of, the conventional stent delivery systems described in Japanese Application Publication No. 2003-62078, Japanese Application Publication No. 2007-135880, etc.

Now, a preferred embodiment of the stent delivery system disclosed here will be described below referring to the drawings. It is to be noted, however, that the present invention is not restricted to the following embodiment.

Figure 2A:
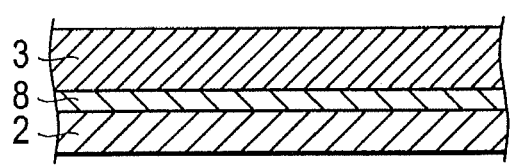
FIG. 2A is an enlarged cross-sectional view of the device taken along the section line 2A-2A in FIG. 1.
Figure 2B:
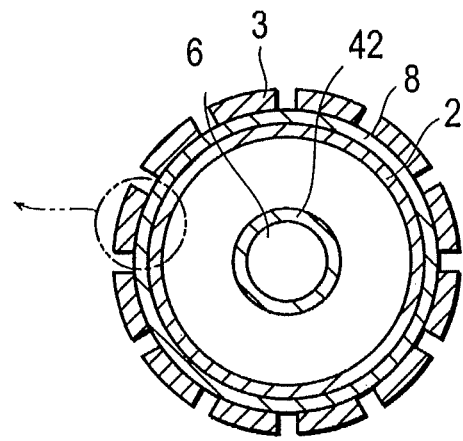
FIG. 2B is an enlarged view of a portion of the longitudinal cross-section of the device shown in FIG. 2A.
Figure 2C:
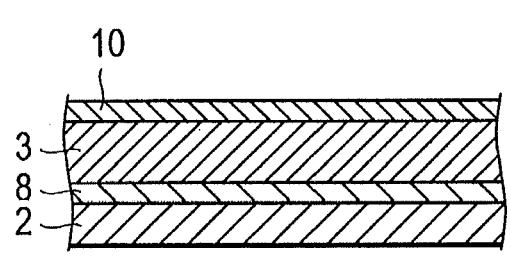
FIG. 2C is an enlarged cross-sectional view of the balloon similar to FIG. 2A, but illustrating an additional variation.
Figure 2D:
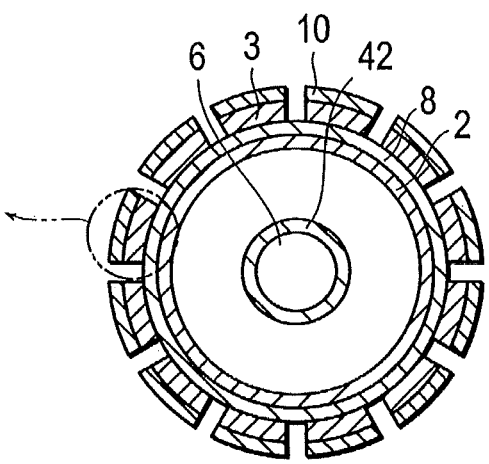
FIG. 2D is an enlarged view of a portion of the longitudinal cross-section of the version of the device shown in FIG. 2C.

Referring initially to FIGS. 1, 2A and 2B, the stent delivery system 1 includes a tube-shaped shaft body 4, a balloon (stent-expanding balloon) 2 provided on a distal portion (tip portion) of the shaft body 4, and a stent 3 so mounted as to encircle the balloon 2. Here, a stent drop-off preventing layer 8 is formed on that surface of the balloon 2 which makes contact with the stent 3. In addition, the shaft body 4 is composed of an outer tube shaft 41 having a balloon inflation lumen 7 communicating with the inside of the balloon 2, and an inner tube shaft 42 having a guide wire lumen 6. The balloon 2 includes an inflatable section (straight tube section) inflated into a tubular shape substantially uniform in outer diameter by a fluid introduced into the inside of the balloon through the balloon inflation lumen 7, tapered sections provided on the proximal side and the distal side relative to the inflatable section and smaller than the inflatable section in outside diameter, and joint sections constant in outside diameter and provided on the proximal side and the distal side relative to the tapered sections. The proximal-side joint section of the balloon 2 is secured to the outer tube shaft 41, while the distal-side joint section is secured to the inner tube shaft 42. The stent delivery system 1 disclosed here is provided with radiopaque markers 5 on the inner tube shaft 42, respectively at positions near the proximal end and near the distal end of the inflatable section of the balloon 2. While the stent delivery system in the present embodiment has two lumens (the guide wire lumen 6 and the balloon inflation lumen 7), this configuration is not restrictive, and the stent delivery system may have more than two lumens, depending on the use of the system.

As shown in FIGS. 1, 2A and 2B, the stent drop-off preventing layer 8 containing a compound with a plurality of thiol groups is formed on a surface of the balloon 2. While the stent drop-off preventing layer 8 is formed on the whole balloon surface in FIGS. 1, 2A and 2B, the stent drop-off preventing layer 8 may not necessarily be formed on the whole balloon surface. It suffices for the stent drop-off preventing layer 8 to be formed on at least a portion of the surface of the balloon 2, specifically, on at least that surface portion of the balloon 2 which makes contact with the stent. This helps ensure that the thiol groups (—SH groups) or disulfide groups (—S—S— groups) derived from the thiol compound in the stent drop-off preventing layer 8 and the metallic portion of the stent 3 are bonded to each other through an interaction. Therefore, simple crimping (diametrical contraction) of the stent 3 on the balloon 2 helps ensure that even if a strong load due to friction is exerted on the stent 3 when the stent 3 is inserted into a stenosed part, the stent 3 can sufficiently endure the load, and the stent 3 can be effectively restrained or prevented from dropping off from, or shifting on, the balloon 2. While the stent 3 may be composed only of the metallic stent body as shown in FIG. 2A, a drug coat layer 10 may be provided on a portion, on the side opposite to the portion making contact with the stent drop-off preventing layer 8, of the stent 3 as shown in FIG. 2B.

The stent delivery system, including each of the component members, will be described in more detail below.

(1) Balloon (Stent-expanding Balloon)

The balloon 2 is a foldable one, and, when not inflated, it is disposed in the folded state on the outer circumference of the inner tube shaft 42. The balloon 2 has the inflatable section (a hollow substantially cylindrical section in FIG. 1) which is a tubular portion (preferably, a hollow cylindrical portion) substantially uniform in outer diameter so that it can expand the stent 3 mounted thereto. The hollow substantially cylindrical section may not necessarily be in the shape of a perfect hollow cylinder but may be in the shape of a polygonal prism. Of the balloon 2, the portions on the proximal side and the distal side relative to the inflatable section are tapered sections smaller in outer diameter than the inflatable section. Further, the portions on the proximal side and the distal side relative to the tapered sections are joint sections which are constant in outside diameter. The proximal-side joint section is secured in a liquid-tight manner to the outer tube shaft 41, while the distal-side joint section is secured in a liquid-tight manner to the inner tube shaft 42, by use of an adhesive or by heat fusing.

It suffices for the balloon 2 to have at least its surface (outer surface) formed from a polymeric material. Here, the expression "to have at least its surface formed from a polymeric material" requires only that at least the surface (outer surface) of the balloon should be composed of a polymeric material; thus, the balloon is not at all restricted to one that is wholly composed (formed) of a polymeric material. Therefore, those balloons in which a balloon core part formed of a hard reinforcing material such as metallic materials and ceramic materials is provided on its surface with a coating of a polymeric material more flexible than the reinforcing material such as metallic materials by an appropriate method (a conventionally known method such as dipping, spraying, coating, printing, etc.), and those balloons in which a metallic material or the like of a balloon core part and a polymeric material of a surface polymer layer are compounded (by an appropriate reaction treatment) to form a surface polymer layer, are also included in the balloon pertaining to the present invention. Accordingly, the balloon core part may be a multilayer structure in which different materials are laminated in multiple layers, a structure (composite) in which members formed of different materials on a part-by-part basis are united, or the like. Between the balloon core part and the surface polymer layer, there may further be formed a middle layer which is different from the core part and the surface polymer layer. Here, the material which can be used for the middle layer is not specifically restricted, and may be appropriately selected according to the intended use. Examples of the material include, but are not restricted to, various metallic materials, various ceramic materials and, further, organic-inorganic composites. Furthermore, the surface polymer layer may also be a multilayer structure in which different polymeric materials are laminated in multiple layers, a structure (composite) in which members formed of different polymeric materials on a part-by-part basis are united, or the like.

In this case, the material which can be used for the balloon core part is not specifically restricted. There can be used reinforcing materials capable of sufficiently exhibiting a function as an optimum balloon core part according to the use of the stent delivery system. Examples of the material include, but are not restricted to, inorganic materials such as various metallic materials, e.g., various stainless steels (SUS) such as SUS304, SUS316L, SUS420J2, SUS630, etc., gold, platinum, silver, copper, nickel, cobalt, titanium, iron, aluminum, tin, nickel-titanium alloys, cobalt-chromium alloys, zinc-tungsten alloys, etc., as well as various ceramic materials, and, further, metal-ceramic composites.

In addition, the polymeric material which can be used for the balloon or the surface polymer layer is not specifically restricted. There can be used those known materials which are generally used in stent delivery systems. Examples of the usable material include polyamide resins, e.g., homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12), etc., copolymers such as caprolactam/laurylolactam copolymer (nylon 6/12), caprolactam/aminoundecanoic acid copolymer (nylon 6/11), caprolactam/w-aminononanoic acid copolymer (nylon 6/9), caprolactam/hexamethylenediammonium adipate copolymer (nylon 6/66), adipic acid-metaxylenediamine copolymer, copolymers of hexamethylenediamine with m- or p-phthalic acid, etc., polyolefins such as polyalkylene resins, e.g., polyethylene resins such as linear low-density polyethylene (LLDPE), low-density polyethylene (LDPE), high-density polyethylene (HDPE), etc., polypropylene resin, etc., ethylene-propylene copolymer, ethylene-vinyl acetate copolymer, and their cross-linked products and partially cross-linked products (e.g., cross-linked ethylene-vinyl acetate copolymer), etc., epoxy resin, urethane resin, diallylphthalate resin (allyl resin), polycarbonate resin, fluoro-resins, amino resins (urea resin, melamine resin, benzoguanamine resin), polyester resins (e.g., polyethylene terephthalate), styrol resin, acrylic resins, polyacetal resin, vinyl acetate resin, phenol resins, vinyl chloride resin, silicone resins (silicon resins), polyarylene sulfides (e.g., polyphenylene sulfide), silicone rubber, latex rubber, and nylon elastomers which are block copolymers having a polyamide such as nylon 6, nylon 66, nylon 11, nylon 12, etc. as a hard segment and having a polyalkylene glycol, polyether, aliphatic polyester or the like as a soft segment. These materials may be used either singly or in combination of two or more of them. In the latter case, the balloon or the surface polymer layer may be in the form of a single layer formed from a mixture of two or more materials, or may be in the form a laminate of the mixture of two or more materials. The polymeric material may be a synthesized product or a commercial product. For instance, exemplary commercial products of the above-mentioned polyamide resins include RILSAN (registered trademark) AECNO TL (nylon 12, produced by ARKEMA K.K.), Grilamid L25 (produced by MSK Japan Ltd.). Exemplary commercial products of the above-mentioned nylon elastomers include Grilflex ELG 5660 and Grilflex ELG6260 (both produced by EMS-CHEMIE Japan Ltd.). For the balloon or the surface polymer layer, there may be used an optimum polymeric material according to the use of the stent delivery system. Among these materials, orientable ones are preferred. The balloon is preferably formed of a biaxially oriented material which has high strength and expansion force. The method for producing the balloon can be appropriately selected from, but is not restricted to, the following known producing methods. Specific examples of the producing method which can be preferably used include such producing methods as blow molding, extrusion, injection molding, rotational molding, blowing, transfer molding, press molding, and solvent casting method. Among these methods, preferred are extrusion, blow molding, and injection molding, and particularly preferred is blow molding.

More specifically, the balloon can be produced by biaxially orienting blow molding as described below. First, a tube (a cylindrical portion) composed of the above-mentioned material is oriented to a predetermined length at an appropriate temperature (for example, 15 to 300 degrees C.). Therefore, the tube is oriented in the axial direction (the longitudinal direction of the stent delivery system). Next, the oriented tube is expanded in a mold, whereby blow molding is performed. The molding space (cavity) in the mold has a shape substantially the same as the shape of the balloon when inflated. In the mold, a high-pressure gas such as nitrogen gas is injected into the tube. In the case of this blow molding, the temperature of the tube is raised by heating the mold, whereby the tube is softened and expanded in the radial direction. Therefore, the tube is oriented in a direction different from the axial direction in which the tube has first been oriented. As a result, a biaxially oriented balloon is obtained. The orientation of the tube in the axial direction may be conducted after the blow molding. Or, alternatively, the orientation of the tube in the axial direction may be performed simultaneously when the tube is expanded in the radial direction in the mold, namely, simultaneously with the blow molding. By such a producing method, it is possible to relatively easily produce a balloon which is rather high in dimensional accuracy and has little dispersions in shape, membrane strength, characteristic properties or the like (e.g., shape, strength, etc. are substantially constant).

The size of the balloon 2 is not particularly limited, and a size similar to those known sizes generally used in stent delivery systems is applied. Specifically, the balloon is so sized that the outside diameter of the hollow cylindrical section (inflatable section) when inflated is preferably 1.5 to 6 mm, more preferably 2 to 4 mm. In addition, the balloon is so sized that the length of the inflatable section (straight tube section) is preferably 5 to 50 mm, more preferably 8 to 40 mm.

(2) Stent Drop-off Preventing Layer

The stent drop-off preventing layer 8 containing a compound with a plurality of thiol groups is formed at least on that surface of the balloon 2 which makes contact with the stent 3, as shown in FIGS. 2A and 2B. The interaction between the thiol groups (—SH groups) or disulfide groups (—S—S— groups) in the stent drop-off preventing layer 8 and the metallic portion of the stent 3 helps ensure that simple crimping (diametrical contraction) of the stent 3 on the balloon 2 results in that even when a strong load due to friction is exerted on the stent 3 at the time of insertion into a stenosed part, the stent 3 can sufficiently endure the load, and the stent 3 can be effectively restrained or prevented from dropping off from, or shifting on the balloon 2. Here, it suffices for the stent drop-off preventing layer 8 to be formed at least on the balloon surface portion that makes contact with the stent 3. The ratio of the area of the stent drop-off preventing layer 8 to the whole surface of the balloon 2 is preferably 20 to 100%, more preferably 100% (a configuration or the state in which the stent drop-off preventing layer 8 is formed on the whole outer surface of the balloon 2).

The method for coating the balloon surface with the thiol compound is not specifically restricted. Examples of the coating method include a method in which a solution containing the thiol compound is applied to the balloon surface and dried, and a method in which the thiol compound is supported on the balloon surface by irradiation with an ionized gas plasma, irradiation with ultraviolet rays, irradiation with electron rays, vacuum evaporation, heating treatment or the like. Among these methods, particularly preferred is the method in which the thiol compound is supported on the balloon surface by irradiation with an ionized gas plasma. In general, a thiol group can react with such reactive functional groups as carboxyl group, hydroxyl group and peroxide (inclusive of functional groups or radicals generated or introduced by a plasma treatment). However, when the thiol compound is only applied to a surface of a layer of a polymeric material (e.g., a polyamide or polyethylene or the like) having no such reactive functional groups, the polymeric material cannot react with (be bonded to) the thiol compound. Therefore, some polymeric materials have the problem that fixation of the thiol compound to the balloon surface is difficult or impossible to achieve by only applying the thiol compound to the balloon surface. On the other hand, in the case where the thiol compound is supported on the balloon surface by irradiation with an ionized gas plasma, even if the polymeric material does not have any reactive functional group, the thiol compound can be firmly bonded (fixed) to the balloon surface. Here, the mechanism by which the firm supporting (fixation) of the thiol compound onto the balloon surface occurs has not been elucidated or determined, but it may be surmised as follows. The system disclosed here is not limited to this surmise. When the balloon surface not yet coated with the thiol compound is irradiated with an ionized gas plasma, it is thereby generally ensured that even if the balloon is formed of a polymeric material which is a polyamide or polyethylene or the like having no functional groups capable of reacting with the thiol compound, functional groups such as carboxyl group, hydroxyl group, or peroxide can be introduced to the balloon surface. As a result, wettability of the balloon surface for wetting with a solution containing the thiol compound dissolved therein is enhanced, so that the balloon surface can be uniformly coated with the thiol compound. In addition, the functional group of the balloon surface and the thiol group of the thiol compound react with each other, whereby the thiol compound can be firmly fixed to the balloon surface. The surface of the polymeric material irradiated with the ionized gas plasma is formed with ruggedness namely, minute projections and recesses on nanometer order. This helps enable an increase in the amount of the thiol compound supported per unit area.

The expression "supporting" used here means the state in which the thiol compound is at least so fixed that it will not easily be freed from the balloon surface. The state may be a state in which the thiol compound has built up on the balloon surface or a state in which the balloon surface is impregnated with the thiol compound.

The thiol compound is not specifically restricted insofar as it is a compound having a plurality of thiol groups in the molecule thereof. Desirably, however, the thiol compound has such a structure that when the balloon surface is subjected to an ionized gas plasma treatment and the subsequent heating treatment or the like to effect a reaction of the thiol compound with the polymeric material of the balloon surface and firm bonding (fixation) of the thiol compound to the balloon surface, the thiol groups remaining at the outermost surface of the thiol compound are easily exposed, in order that the remaining thiol groups will easily interact with the metallic portion of the stent. From such a viewpoint, it suffices for the thiol compound to be a compound which has at least two thiol groups in its molecule. When the number of the thiol groups present in the molecule is increased, the crosslink density of the stent drop-off preventing layer formed is enhanced, and the thiol compound can interact with the metallic portion of the stent more firmly, which is favorable. Accordingly, the thiol compound is preferably a compound having 2 to 10 thiol groups, more preferably 3 to 6 thiol groups, in the molecule thereof.

From this point of view, the thiol compound may be any of straight-chain ones, branched-chain ones and cyclic ones. Preferable examples of such thiol compound include: compounds having two thiol groups in the molecule thereof, such as 1,2-ethanedithiol, 1,2-propanedithiol, 1,3-propanedithiol, 1,4-butanedithiol, 2,3-butanedithiol, 1,5-pentanedithiol, 1,6-hexanedithiol, 1,8-octanedithiol, 3,6-dioxa-1,8-octanedithiol, bis(2-mercaptoethyl)ether, bis(2-mercaptoethyl) sulfide, 1,2-benzenedithiol, 1,4-benzenedithiol, 1,4-bis(mercaptomethyl)benzene, toluene-3,4-dithiol, 1,5-dimercaptonaphthalene, 2,6-dimercaptopurine, 4,4'-biphenyldithiol, 4,4'-thiobisbenzenethiol, tetraethylene glycol bis(3-mercaptopropionate), etc.; compounds having three thiol groups in the molecule thereof, such as 1,3,5-benzenetrithiol, tris[(3-mercaptopropionyloxy)ethyl] isocyanurate (TEMPIC), triazinetrithiol, trimethylolpropane tris(3-mercaptopropionate) (TMMP), etc.; compounds having four thiol groups in the molecule thereof, such as pentaerythritol tetrakis(mercaptoacetate), pentaerythritol tetrakis(3-mercaptopropionate) (PEMP), pentaerythritol tetrakis(3-mercaptobutyrate), etc.; compounds having six thiol groups in the molecule thereof, such as dipentaerythritol hexakis(3-mercaptopropionate), etc.; and their derivatives and polymers. Preferably, use is made of any of tris[(3-mercaptopropionyloxy)ethyl] isocyanurate, pentaerythritol tetrakis(3-mercaptopropionate), and dipentaerythritol hexakis(3-mercaptopropionate), which are compounds having 3 to 6 thiol groups, having a stable molecular skeleton, having a good affinity for the balloon surface, and having such a structure that when the thiol groups are bonded to the balloon surface, the remaining thiol groups are easily exposed at the outermost surface. These thiol compounds may be used either singly or in combination of two or more of them. Here, by combining the use of thiol compounds having different numbers of thiol groups, it is possible to control the crosslink density of the stent drop-off preventing layer. Here, the combination of the thiol compounds is not specifically restricted. Preferable examples of the combination include a combination of a compound having two thiol groups in its molecule with a compound having three thiol groups in its molecule, a combination of a compound having two thiol groups in its molecule with a compound having four thiol groups in its molecule, and a combination of a compound having three thiol groups in its molecule with a compound having four thiol groups in its molecule. Therefore, it is possible to appropriately control (raise) the crosslink density of the stent drop-off preventing layer, and to effect firmer interaction (bonding) of the stent drop-off preventing layer with (to) the stent (metallic portion).

In the present embodiment, the thiol compound is not restricted in any way to the above-mentioned thiol compounds. Thus, thiol compounds other than those identified above can also be utilized insofar as they can effectively exhibit the advantageous effect consistent with the disclosure here.

In addition, the coating thickness (after dried) of the thiol compound is not particularly limited. It suffices for the coating thickness to be such a thickness that the coating interacts with the metallic portion of the stent and can restrain or prevent shifting or drop-off of the stent from the balloon under a strong load due to friction. Ordinarily, the thickness is not more than 10 µm, preferably not more than 1 µm. In addition, a state in which a monomolecular membrane layer of the thiol compound (one molecule of the thiol compound in the thickness direction) is formed on the balloon surface may be adopted, provided that the thiol compound can effectively function as a so-called molecular adhesive. Furthermore, from the viewpoint that the stent delivery system can be made thinner (smaller in diametrical size) by reducing the thickness of the thiol compound, a state in which the balloon surface is impregnated with the thiol compound may be adopted.

In the method for supporting the thiol compound on the balloon surface by irradiation with an ionized gas plasma (plasma treatment), specific examples of the mode (manner) for fixing the thiol compound to the balloon include (i) a mode in which application of a solution containing the compound having thiol groups dissolved therein to the balloon surface is preceded by irradiation of the balloon surface with an ionized gas plasma so as to support the compound having thiol groups on the balloon surface. In this mode, specifically, prior to the application of the solution containing the thiol compound dissolved therein (thiol compound solution) to the balloon surface (prior to coating with the thiol compound), the balloon surface is preliminarily subjected to a plasma treatment so as to modify or activate the surface, and, thereafter, the thiol compound solution is applied, so as to effect a reaction (bonding, or fixation) between the thiol compound and the balloon surface. In this mode, the thiol compound can be firmly fixed to the balloon surface. In general, the thiol group possessed by the thiol compound can react with reactive functional groups such as carboxyl group, hydroxyl group or peroxide (inclusive of the functional groups or radicals generated or introduced by the plasma treatment). However, when the balloon surface made of a polymeric material (e.g., a polyamide or polyethylene) having no such reactive functional group is only coated with the thiol compound, the polymeric material cannot react with (be bonded to) the thiol compound. Therefore, the thiol compound cannot be firmly fixed to the balloon surface, and peeling of the stent drop-off preventing layer from the balloon may easily occur. According to the above-mentioned mode, on the other hand, the plasma treatment is conducted prior to the application of the thiol compound. This helps ensure that even if the balloon is formed of a polymeric material having no reactive functional group, such as a polyamide or polyethylene, an effect of modifying or activating the balloon surface and/or an effect of enhancing the wettability of the balloon surface for wetting with the thiol compound solution can be obtained. These effects make it possible to generally uniformly apply the thiol compound solution to the balloon surface, and to firmly bond (fix) the thiol compound to the balloon.

In addition, in the above-mentioned mode (i), a heating treatment or the like may be conducted after the application of the thiol compound solution. By conducting a heating treatment or the like after the application of the thiol compound solution, it is possible to accelerate the reaction between the balloon surface and the thiol compound, or to polymerize the thiol compound(s). Consequently, the thiol compound can be fixed to the balloon surface more firmly by the heating treatment or the like.

Also, specific examples of the mode for fixing the thiol compound to the balloon include (ii) a mode in which the solution containing the compound having thiol groups dissolved therein is applied to the balloon surface, followed by irradiation with an ionized gas plasma, so as to support the compound having the thiol groups on the balloon surface. In this mode, specifically, the plasma treatment is conducted after the application of the thiol compound solution to the balloon surface (after coating with the thiol compound), whereby a reaction (bonding) between the thiol compound and the balloon surface is effected. By this mode, also, the thiol compound can be firmly fixed to the balloon surface by irradiation with the ionized gas plasma.

In the above-mentioned mode (ii), the irradiation with an ionized gas plasma may be followed by a heating treatment or the like. With the heating treatment or the like conducted after the plasma treatment, it is possible to accelerate the reaction between the balloon surface and the thiol compound, or to polymerize the thiol compound(s). Accordingly, the thiol compound can be fixed to the balloon surface more firmly by the heating treatment or the like.

Furthermore, specific examples of the mode for fixing the thiol compound to the balloon include a mode in which the plasma treatment before the application of the thiol compound in the above-mentioned mode (i) and the plasma treatment after the application of the thiol compound in the above-mentioned mode (ii) are jointly conducted. This is (iii) a mode in which the balloon surface is irradiated with an ionized gas plasma, then the solution containing the compound having thiol groups dissolved therein is applied to the balloon surface, and irradiation with an ionized gas plasma is again conducted, whereby the compound having the thiol groups is supported on the balloon. In this mode, specifically, prior to the application of the thiol compound, the balloon surface is subjected to a plasma treatment so as to modify or activate the surface, thereafter the thiol compound solution is applied, and then a plasma treatment is again conducted, whereby a reaction (bonding) between the thiol compound and the balloon surface is effected. This mode is excellent in that the thiol compound can be fixed to the balloon surface very firmly.

In this case, also, each of the plasma treatments may be followed by a heating treatment or the like. By such a heating treatment or the like, it is possible to accelerate the reaction between the balloon surface and the thiol compound, or to polymerize the thiol compound(s). Consequently, the thiol compound can be fixed to the balloon surface more firmly by the heating treatment or the like.

The effect of the plasma treatment in any of the above-mentioned modes (i) to (iii) resides in acceleration of the reaction of the thiol compound with the polymeric material forming the balloon surface. Specifically, the plasma irradiation causes generation or emission of ion or electron beams as a result of ionization, whereby the bonds in the polymeric material of the balloon surface under treatment (e.g., the backbone chain of the polymer) are cut or radicals are generated, and the thiol compound (thiol group) reacts with the part having undergone the bond cutting or radical generation. For instance, the polymer part having undergone the bond cutting or radical generation is brought to oxidation or the like, whereby a reactive group such as peroxide is introduced, and the thiol compound can react with (be bonded to) the reactive group. As a result, it can be said, the balloon surface and the thiol compound can be firmly fixed to each other. Now, the above-mentioned mode (iii) in which the above-mentioned modes (i) and (ii) are jointly adopted will be described in more detail below.

(2-1) Plasma Treatment Before Application of Thiol Compound

In the present mode, prior to the application of the thiol compound solution to the balloon (prior to coating with the thiol compound), the balloon surface is preliminarily irradiated with an ionized gas plasma. Therefore, the balloon surface can be modified or activated and the wettability of the balloon surface for wetting with the thiol compound solution can be enhanced. Consequently, the thiol compound solution can be relatively uniformly applied to the balloon surface.

Before the balloon surface is preliminarily irradiated with an ionized gas plasma, the balloon surface may be cleaned by an appropriate method. Specifically, before the wettability of the balloon surface is enhanced by irradiation with an ionized gas plasma, oil or fat and dirt and the like deposited on the polymeric material of the balloon surface are desirably removed. Even in the case where the thiol compound is applied without conducting a plasma treatment prior to the thiol compound application as in the above-mentioned mode (ii), the cleaning treatment is preferably carried out prior to the application of the thiol compound solution.

The pressure condition under which the plasma treatment prior to the thiol compound application is to be conducted is not particularly limited, and may be a reduced pressure or the atmospheric pressure. It is preferable to carry out the plasma treatment under the atmospheric pressure, since the irradiation with a plasma gas can be conducted at a free angle, the system for the treatment can be reduced in size because of the absence of need for a vacuum device, the system configuration can be realized with space saving and at low cost, and the system is excellent from an economic point of view. In addition, by conducting irradiation with a plasma gas while rotating a plasma irradiation nozzle about the work to be treated (balloon), the whole circumference of the work to be treated can be plasma treated uniformly.

Examples of the ionized gas which can be used in the plasma treatment prior to the thiol compound application include helium, neon, argon, krypton, carbon dioxide, carbon monoxide, water vapor, nitrogen, oxygen, and hydrogen. These ionized gases may be used either singly or in combination of two or more of them.

The irradiation time in the plasma treatment prior to the thiol compound application is not more than 10 minutes, preferably in the range of 0.1 second to 1 minute, and more preferably in the range of 1 to 40 seconds. If the plasma irradiation time is below 0.1 second, it may be difficult to secure a period of time for sufficiently enhancing the wettability (modification, activation) of the balloon surface, and it may be difficult to form a very thin coat (monomolecular coat) of the thiol compound solution. If the plasma irradiation time is above 10 minutes, on the other hand, the balloon surface would be activated excessively, so that the cutting of the bonds in the polymeric material of the balloon surface and re-bonding (rearrangement of molecular structure or crosslinking) may occur excessively.

The temperature of the work to be treated (the balloon before coated with the thiol compound) in the plasma treatment prior to the thiol compound application is not particularly limited, as long as it is lower than the melting point of the polymeric material of the balloon surface and it is in such a range that the balloon is not deformed. The temperature may be normal temperature, or may be set high or low by heating or cooling. From an economic point of view, a temperature (5 to 35 degrees C.) obtained without need for a heating device or a cooling device is preferably adopted.

The applied current, gas flow rate and the like in the plasma treatment prior to the thiol compound application are not particularly limited, and may be appropriately determined according to the area of the work to be treated as well as the plasma irradiation system and the species of the ionized gas which are used (see, for example, Example 1).

The plasma irradiation system which can be used for the plasma treatment prior to the thiol compound application is not specifically restricted. Examples of the plasma irradiation system which can be used include a plasma irradiation system which includes a plasma generation pipe for introducing gas molecules and exciting the gas molecules to generate a plasma, and electrodes for exciting the gas molecules in the plasma generation pipe, and in which a plasma is released from one end of the plasma generation pipe. The plasma irradiation system, however, is not restricted in any way to the just-mentioned configuration. For instance, an ionized gas plasma irradiation system suitable for irradiation of the balloon, particularly a plasma irradiation system designed for plasma irradiation at the atmospheric pressure, selected from the conventionally commercialized ones can be used. Specific examples of the commercialized plasma irradiation system which can be utilized include, but are not restricted in any way to, a plasma irradiation system DURADYNE (trade name or trademark) produced by TRI-STAR TECHNOLOGIES, and a plasma irradiation system PLASMABEAM produced by DIENER ELECTRONIC.

In the disclosure here, the plasma treatment may be carried out either only once or repeatedly two or more times. In the latter case, the plasma treating conditions in each plasma treating step may be the same or different.

(2-2) Application of Thiol Compound

The method for applying the thiol compound solution to the balloon surface is not specifically restricted, and there can be used conventionally known methods such as an applying or printing method (coating method), a dipping method, a spraying method, a spin coating method, and a mixed solution-impregnated sponge coating method.

Prior to the application of the thiol compound solution to the balloon surface, a treatment by which the fixation of the stent drop-off preventing layer to the balloon is made firmer (hereinafter referred to also as "fixation-strengthening treatment") may be applied to the balloon. Here, a substance to be used for the fixation-strengthening treatment (hereinafter referred to also as "fixation-strengthening agent") is not specifically restricted, and examples of the substance include butylated hydroxyanisole (BHA) and resorcinol. By such a fixation-strengthening agent, the thiol compound can be clamped in the balloon structure more efficiently, and fixation of the stent drop-off preventing layer to the balloon can be made firmer. In addition, the method for fixation-strengthening treatment of the balloon is not specifically restricted. For instance, there can be used a method in which the balloon is immersed in a solution that contains the fixation-strengthening agent. Here, the solvent for dissolving the fixation-strengthening agent is not particularly restricted, so long as it can dissolve the fixation-strengthening agent. The solvent can be appropriately selected according to the kind of the fixation-strengthening agent used. Examples of the solvent include methanol, ethanol, and isopropanol. In addition, the conditions for treatment of the balloon with the fixation-strengthening agent are not particularly limited. For instance, it is preferable to immerse the balloon in the solution containing the fixation-strengthening agent at 5 to 50 degrees C. for 0.5 to 20 minutes, more preferably at 20 to 40 degrees C. for 1 to 10 minutes. By such a treatment, the thiol compound can be clamped in the balloon structure more efficiently, and the fixation of the stent drop-off preventing layer onto the balloon can be made firmer. Where the treatment with the fixation-strengthening agent is conducted, therefore, the above-mentioned plasma treatment prior to the thiol compound application can be omitted.

Now, the system disclosed here will be described in detail below while taking as an example a mode in which a balloon is immersed in a thiol compound solution and then dried to coat the balloon surface with the thiol compound solution, followed by a plasma treatment, and then a heating treatment or the like is further conducted, to thereby fix the thiol compound to the balloon surface. It should be noted here, however, that the present invention is not restricted in any way to this described mode.

In addition, in the case where the thiol compound is fixed to only a part of the balloon surface, it is possible, by coating only a part of the balloon with the thiol compound solution (through immersion and drying), then conducting again irradiation with an ionized gas plasma and further conducting a heating treatment or the like as required, to fix the thiol compound to a desired surface portion of the balloon.

In the case where it is difficult to immerse only a part of the balloon surface in the thiol compound solution, a method as follows may be adopted. First, a balloon surface portion to which the thiol compound is not to be fixed is preliminarily protected (e.g., covered) with a detachable appropriate member or material or a stent. Then, the balloon in this state is immersed in the thiol compound solution and is dried, followed again by irradiation with an ionized gas plasma. Further, if necessary, a heating treatment or the like is conducted, after which the protective member (material) on the balloon surface portion to which the thiol compound is not to be fixed is detached. By such a method, the thiol compound can be fixed to the desired surface part of the balloon. In the case where preliminary protection with a stent is conducted, the stent is mounted onto the balloon, and, therefore, it is unnecessary to detach the stent. It is to be noted, however, that the present invention is not restricted to such a method in any way, and the fixation of the thiol compound can be carried out by appropriately utilizing a conventionally known method. For instance, in the case where it is difficult to immerse only a part of the balloon in the thiol compound solution, coating techniques (e.g., applying method, spraying method, etc.) other than immersion (dipping) method may be applied.

The concentration of the thiol compound solution used in applying the thiol compound is not particularly limited. From the viewpoint of uniform coating in a desired thickness, the concentration of the thiol compound in the thiol compound solution is preferably 0.001 to 30 wt %, more preferably 0.01 to 10 wt %. If the concentration of the thiol compound is below 0.001 wt %, it may be impossible to fix a sufficient quantity of the thiol compound to the balloon surface. If the concentration of the thiol compound is above 30 wt %, on the other hand, the viscosity of the thiol compound solution may be so high that the thiol compound cannot be fixed in a uniform thickness or that it is difficult to speedily apply the thiol compound solution to the balloon surface. It should be noted here, however, that a thiol compound concentration outside the above-mentioned range can sufficiently be used insofar as it does not influence the advantageous effect of the present invention.

Examples of the solvent to be used for the thiol compound solution include, but are not restricted in any way to: water; alcohols such as methanol, ethanol, isopropanol, ethylene glycol, etc.; ketones such as acetone, methyl ethyl ketone, etc.; esters such as ethyl acetate, etc.; halides such as chloroform, etc.; olefins such as hexane, etc.; ethers such as tetrahydrofuran (THF), butyl ether, etc.; aromatic solvents such as benzene, toluene, etc.; and amides such as N,N-dimethylformamide (DMF), etc. These solvents may be used either singly or in combination of two or more of them.

The drying conditions after the immersion of the balloon in the thiol compound solution are not particularly limited. Specifically, the balloon as an object of drying is very small and it takes little time to dry the balloon; therefore, even natural drying may be sufficient. From such a point of view, the drying temperature for the thiol compound solution is 20 to 150 degrees C., preferably 20 to 130 degrees C., and the drying time is 1 second to 1 hour, preferably 1 to 30 minutes. If the drying time is below 1 second, the plasma treatment after application of the thiol compound would be carried out in an undried state. This results in the energy of the plasma being absorbed in evaporation of the remaining solvent or the like, so that it may be difficult to sufficiently achieve the activation of the balloon surface or the thiol compound (for example, enhancement of the surface energy of the balloon, or creation of functional groups (active spots or active sites) through excitation or ionization or the like of the elements of the balloon surface and/or the thiol compound). Also, it may be impossible to sufficiently secure bonding parts for bonding to the balloon surface. If the drying time is above 1 hour, on the other hand, a further effect owing to drying for a longer time than the above-mentioned cannot be obtained, so that such long drying is uneconomical.

The pressure condition during drying is also not particularly restricted. The drying may be conducted under normal pressure (atmospheric pressure), or may be performed under a raised pressure or a reduced pressure.

As drying means (device), there can be used, for example, an oven or a vacuum dryer or the like. In the case of natural drying, drying means (device) is not particularly needed.

The steps of immersing the balloon in the thiol compound solution, drying the balloon to thereby coat the balloon surface with the thiol compound solution, then conducting the plasma treatment and further carrying out the heating treatment may be carried out only once or repeatedly two or more times. In the latter case, the conditions in each of the treating steps (the concentration of the thiol compound in the thiol compound solution, the immersion conditions, the drying conditions, the coating conditions, the plasma treatment conditions, etc.) may be the same or different.

(2-3) Plasma Treatment after Application of Thiol Compound

In the present embodiment, after the thiol compound solution is applied to the balloon surface, irradiation with an ionized gas plasma is conducted again. By such a plasma treatment, also, the thiol compound and the balloon surface can be activated, bonding (reaction) between the thiol compound and the balloon surface can be effected, and the thiol compound can be fixed relatively firmly. In addition, polymerization of the thiol compound(s) can also be effected by the plasma treatment. Or, alternatively, where irradiation with an ionized gas plasma that contains oxygen is conducted, the thiol compound and the balloon surface can be activated, a reaction between the thiol compound and the balloon surface can be brought about, the thiol compound can be relatively firmly fixed to the balloon surface, and an oxidation reaction between the thiol compound(s) can be accelerated, whereby the strength of the stent drop-off preventing layer on the balloon can be enhanced.

The plasma treatment after the application of the thiol compound in this embodiment can be carried out under the same conditions as the above-mentioned plasma treatment before the application of the thiol compound, and can be conducted by use of the same plasma irradiation system as that used in the plasma treatment before the thiol compound application. The conditions of the plasma treatment after the thiol compound application in this embodiment may not necessarily be the same as those of the plasma treatment before the thiol compound application.

The plasma treatment may be performed only once or repeatedly two or more times. In the latter case, the plasma treatment conditions in each plasma treatment step may be the same or different.

In order that polymerization of the thiol compound(s) can be accelerated in the plasma treatment after the thiol compound application in the present embodiment, a photoinitiator may be added to the thiol compound solution with an appropriate timing and in an appropriate amount. This helps ensure that the efficiency of reaction (polymerization) can be further enhanced by light emission during the plasma treatment, and a firmer stent drop-off preventing layer can be formed. Here, the photoinitiator is not specifically restricted. Examples of the photoinitiator which can be used include ketal photoinitiators, acetophenone photoinitiators, benzoin ether photoinitiators, acylphosphine oxide photoinitiators, α-ketol photoinitiators, aromatic sulfonyl chloride photoinitiators, photoactive oxime photoinitiators, benzoin photoinitiators, benzil photoinitiators, benzophenone photoinitiators, and thioxanthone photoinitiators. These photoinitiators may be used either singly or in combination of two or more of them. Examples of the ketal photoinitiators include 2,2-dimethoxy-1,2-diphenylethan-1-one [for example, trade name "Irgacure 651" (produced by Ciba Japan)]. Examples of the acetophenone photoinitiators include 1-hydroxycyclohexyl phenyl ketone [for example, trade named "Irgacure 184" (produced by Ciba Japan)], 2,2-diethoxyacetophenone, 2,2-dimethoxy-2-phenylacetophenone, 4-phenoxydichloroacetophenone, and 4-(t-butyl)dichloroacetophenone. Examples of the benzoin ether photoinitiators include benzoin methyl ether, benzoin ethyl ether, benzoin propyl ether, benzoin isopropyl ether, and benzoin isobutyl ether. Examples of the acylphosphine oxide photoinitiators include trade name "Lucirin TPO" (produced by BASF). Examples of the α-ketol photoinitiators include 2-methyl-2-hydroxypropiophenone, and 1-[4-(2-hydroxyethyl)phenyl]-2-methylpropan-1-one. Examples of the aromatic sulfonyl chloride photoinitiators include 2-naphthalenesulfonyl chloride. Examples of the photoactive oxime photoinitiators include 1-phentyl-1,1-propandione-2-(o-ethoxycarbonyl) oxime. Examples of the benzoin photoinitiators include benzoin. Examples of benzil photoinitiators include benzil. Examples of the benzophenone photoinitiators include benzophenone, benzoylbenzoic acid, 3,3'-dimethyl-4-methoxybenzophenone, polyvinylbenzophenone, and α-hydroxycyclohexyl phenyl ketone. Examples of the thioxanthone photoinitiators include thioxanthone, 2-chlorothioxanthone, 2-methylthioxanthone, 2,4-dimethylthioxanthone, isopropylthioxanthone, 2,4-diisopropylthioxanthone, and dodecylthioxanthone.

(2-4) Heating Treatment in Fixation of Thiol Compound

In fixing the thiol compound to the balloon surface, acceleration of the reaction between the balloon surface and the thiol compound or acceleration of the polymerization of the thiol compound(s) may be effected by further conducting a heating treatment or the like, after the plasma treatment is conducted following the application of the thiol compound.

Treatment conditions for such a heating treatment are not specifically restricted insofar as they enable acceleration of the reaction (polymerization) of the thiol compound(s), and the conditions may be appropriately determined according to the temperature characteristics (thermal resistance) of the polymeric material constituting the balloon surface.

Therefore, the lower limit for the heating treatment temperature (a set temperature for a heating device such as a heating furnace) is not lower than the temperature enabling acceleration of the reaction (polymerization) of the thiol compound(s), preferably not lower than 40 degrees C., more preferably not lower than 50 degrees C. When the heating treatment temperature is below the temperature enabling acceleration of the reaction (polymerization) of the thiol compound(s), the desired reaction is not accelerated sufficiently. In such a situation, it may take a long time to complete the heating treatment, which is uneconomical, or the reaction (polymerization) may not be preceded by the heating treatment, so that it may be impossible to obtain the desired effect.

In addition, an upper limit for the heating treatment temperature is not more than the temperature which is 5 degrees C. lower than the melting point of the polymeric material constituting the balloon surface, and is preferably not more than the temperature which is 10 degrees C. lower than the melting point. Where the heating treatment temperature is higher than the temperature which is 5 degrees C. lower than the melting point of the polymeric material constituting the balloon surface, the reaction (polymerization) is sufficiently accelerated on one hand. On the other hand, a temperature higher than the set temperature may be generated depending on the temperature distribution in the inside of the heating device such as a heating furnace, which may lead to melting or deformation of a part of the balloon surface.

Some polymeric materials for use to form the balloon surface will be taken as examples, and an example of the range of the heating treatment temperature will be shown below, but the range of the heating treatment temperature in this embodiment is not limited in any way to these examples. For instance, where the polymeric material constituting the balloon surface is a polyamide resin (nylon 6, 11, 12, or 66 or the like), the heating treatment temperature is preferably 40 to 150 degrees C., more preferably 40 to 140 degrees C. Where the polymeric material constituting the balloon surface is a polyethylene (LDPE, LLDPE, HDPE or the like), the heating treatment temperature is preferably 40 to 85 degrees C., more preferably 50 to 80 degrees C.

The heating treatment time is not particularly limited insofar as it enables acceleration of the reaction (polymerization) of the thiol compound(s), and is preferably 15 minutes to 24 hours, more preferably 30 minutes to 12 hours. When the heating time is below 15 minutes, the reaction (polymerization) may not be accelerated sufficiently, and the amount of unreacted thiol compound may increase. As a result, the part bonded to the balloon surface may be secured insufficiently, or the strength-supplementing effect of the polymerization of the thiol compound(s) itself may be exhibited insufficiently. When the heating temperature is above 24 hours, a further effect due to the heating for a longer time than the above-mentioned is not obtained, so that such a long heating is uneconomical.

It should be noted here, however, that the same reaction (polymerization) as in the heating treatment may take place during the plasma treatment after the thiol compound application, and, therefore, it is desirable to appropriately determine the heating treatment temperature and time while taking into account the conditions of the plasma treatment.

The pressure condition in the heating treatment is also not specifically restricted. The heating treatment may be carried out under normal pressure (atmospheric pressure) or may be conducted under a raised pressure or a reduced pressure. Examples of the heating means (device) which can be used include ovens, dryers, and microwave heaters.

In the case where the thiol compound(s) is polymerized, an additive such as a thermopolymerization initiator may be added to the thiol compound solution with an appropriate timing and in an appropriate amount, in order that the polymerization can be accelerated. By the addition, the reaction (polymerization) efficiency is further enhanced, whereby a stronger stent drop-off preventing layer can be formed. Here, the thermopolymerization initiator is not specifically restricted. Examples of the thermopolymerization initiator include: azo compounds (azo initiators) such as 2,2'-azobisisobutyronitrile, 2,2'-azobis-2-methylbutyronitrile, 2,2'-azobis(2-methylpropionate)dimethyl, 4,4'-azobis-4-cyanovalerianic acid, azobisisovaleronitrile, 2,2'-azobis(2-amidinopropane)dihydrochloride, 2,2'-azobis[2-(5-methyl-2-imidazolin-2-yl)propane]dihydrochloride, 2,2'-azobis(2-methylpropionamidine)disulfate, 2,2'-azobis(N,N'-dimethyleneisobutyramidine)dihydrochloride, 2,2'-azobis[N-(2-carboxyethyl)-2-methylpropionamidine]hydrate, etc.; persulfates such as potassium persulfate, ammonium persulfate, etc.; peroxides (peroxide initiators) such as dibenzoyl peroxide, tert-butyl permaleate, t-butyl hydroperoxide, hydrogen peroxide, etc.; substituted ethane initiators such as phenyl-substituted ethane, etc.; and redox initiators such as persulfate-sodium hydrogensulfite mixed agents, peroxide-sodium ascorbate mixed agents, etc. Thermopolymerization conditions are not particularly limited, and can be appropriately selected, taking into account the desired strength of the stent drop-off preventing layer and the like.

Examples of methods other than the heating treatment for accelerating the reaction or polymerization of the thiol compound(s) include irradiation with UV rays, and irradiation with electron beams, which are not restrictive of the methods.

After the fixation of the thiol compound, surplus thiol compound may be cleaned with an appropriate solvent so that only the thiol compound bonded to the balloon surface is left in situ.

After the stent drop-off preventing layer containing the thiol compound is formed on the balloon surface in the above-mentioned manner, the stent is crimped (diametrically contracted) on the balloon. Here, after the stent is crimped on the balloon, a heating treatment may be conducted. By such a heating treatment, the bonding between the stent drop-off preventing layer and the metallic portion of the stent by an interaction is accelerated smoothly.

Here, the treatment conditions in the case where a heating treatment is conducted after the crimping of the stent onto the balloon are not particularly limited. For instance, where the balloon is formed of a polyamide resin (nylon 6, 11, 12, or 66 or the like), the heating treatment temperature is preferably 30 to 150 degrees C., more preferably 40 to 140 degrees C. Where the balloon is formed from a polyethylene (LDPE, LLDPE, HDPE or the like), the heating treatment temperature is preferably 40 to 85 degrees C., more preferably 50 to 80 degrees C. The heating treatment time is preferably 15 minutes to 24 hours, more preferably 30 minutes to 12 hours. Under such heating treatment conditions, the bonding between the stent drop-off preventing layer and the metallic portion of the stent by an interaction is accelerated smoothly.

(3) Stent

Figure 3:
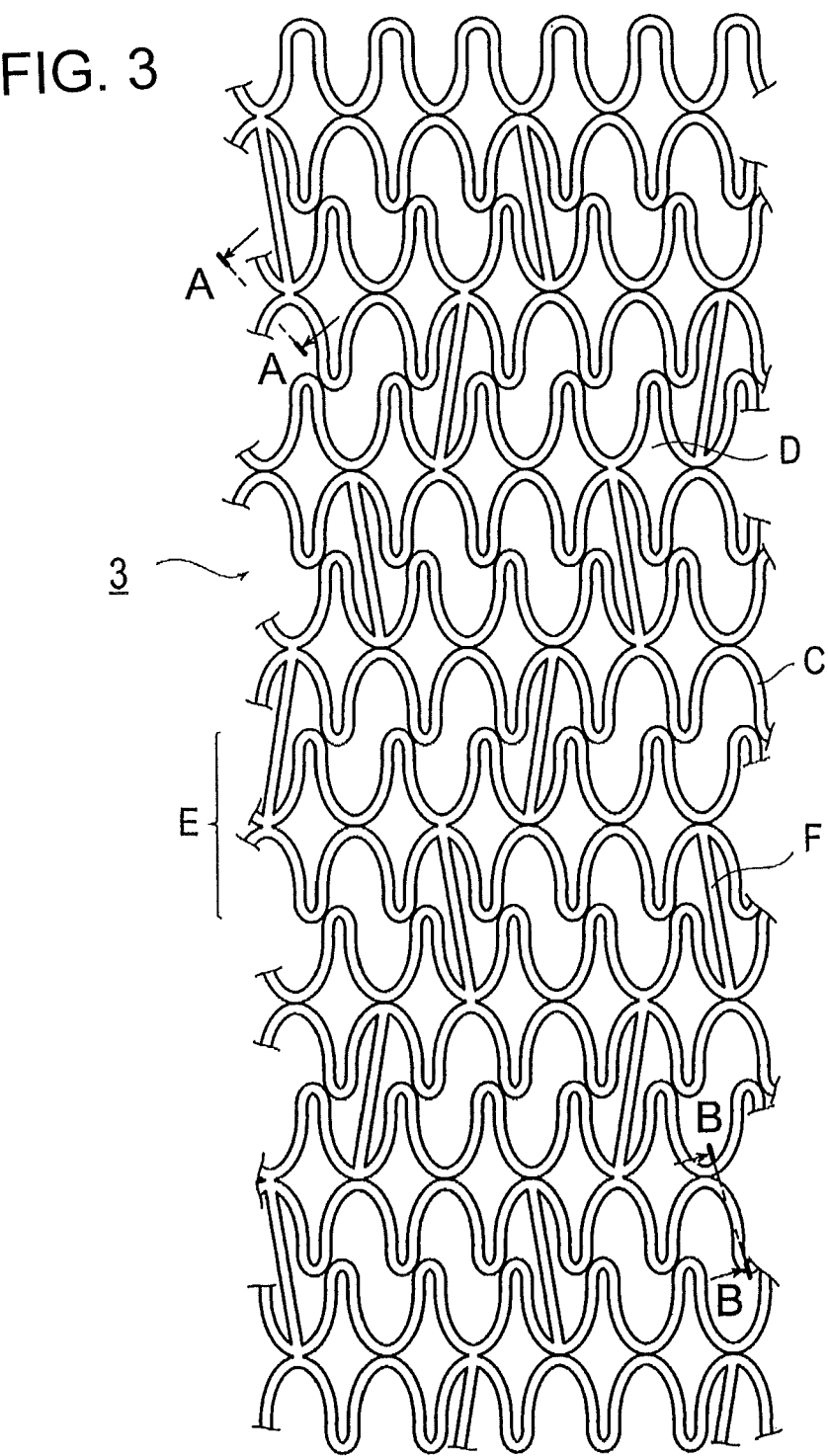
FIG. 3 is a side view showing an embodiment of a stent disclosed here having useful application with the stent delivery device disclosed here.
Figure 4:
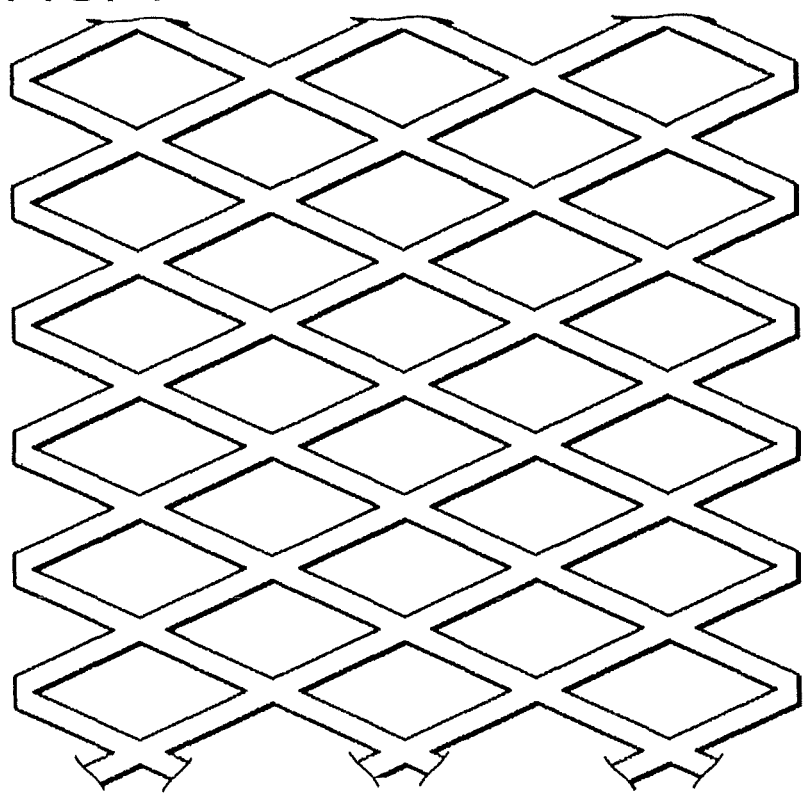
FIG. 4 is a side view showing another embodiment of the stent disclosed here having useful application with the stent delivery device disclosed here.

The shape of the stent 3 used in the system disclosed here is not particularly restricted as long as the stent 3 has a strength sufficient for stable indwelling of the stent 3 in a living body lumen. Examples of the stent shape include a hollow cylindrical body formed by knitting of fibers, and a tubular body formed with minute pores. The stent according to this embodiment is a balloon-expandable one. As shown in FIG. 3, preferably, the stent (main body) 3 is a hollow cylindrical body which is open at both terminal end portions and which extends in the longitudinal direction between the end portions. A side surface of the hollow cylindrical body is provided with a multiplicity of cutouts through which the outside surface of the stent and the inside surface of the stent communicate with each other. With the cutouts deformed, the stent can be expanded and contracted in the radial direction of the hollow cylindrical body. The stent is put indwelling (indwelled) in a living body lumen such as a blood vessel or bile duct, and maintains its shape. In the embodiment shown in FIG. 3, the stent (main body) has a roughly rhombic element D provided therein with the cutout, as a basic element. A plurality of the roughly rhombic elements D are bonded to each other, with the roughly rhombic shapes arranged continuously in the minor axis direction, to form an annular unit E. Each annular unit E is connected with the axially adjacent annular unit through a linear link member F. Therefore, the plural annular units E are arranged continuously in the axial direction in the state of being partly connected with one another. With such a configuration, the stent (main body) is in the form of a hollow cylindrical body which is open at both terminal end portions and extends in the longitudinal direction between the end portions. The side surface of the hollow cylindrical body is provided with the roughly rhombic cutouts. With the cutouts deformed, the stent can be expanded and contracted in the radial direction of the hollow cylindrical body. It is to be noted, however, that the structure of the stent is not restricted to the embodiment shown in the figure. The stent structure has a concept widely including the structures of a hollow cylindrical body open at both terminal end portions and extending in the longitudinal direction between the end portions, wherein the side surface is provided with a multiplicity of cutouts through which the outside surface of the stent and the inside surface of the stent communicate with each other, and the hollow cylindrical body can be expanded and contacted in the radial direction of the stent. Thus, a coiled shape is also included in the concept disclosed here. The sectional shape of the linear material constituting the stent (main body) is also not specifically restricted, and may be any one of rectangles, circle, ellipses, other polygons, etc. In addition to the above-mentioned, other preferred examples of the stent 3 include a stent with a lattice structure as shown in FIG. 4.

In addition, the size of the stent (main body) may be appropriately selected according to the site of application of the stent. The outside diameter of the stent before expansion thereof is preferably 1.0 to 5.0 mm, more preferably 1.50 to 4.50 mm. The length of the stent is preferably 5 to 100 mm, more preferably 7 to 50 mm. In addition, the wall thickness of the stent is not particularly limited insofar as the stent has a radial force required for the stent to be put indwelling in a stenosed part and the stent does not hinder the flow of blood. For instance, the wall thickness of the stent is preferably 1 to 1000 μm, more preferably 50 to 300 μm.

Examples of the material forming the stent 3 include various metallic materials such as various stainless steels (SUS) such as SUS304, SUS316L, SUS420J2, SUS630, etc., gold, platinum, silver, copper, tantalum, nickel, cobalt, titanium, iron, aluminum, tin, nickel-titanium alloys, cobalt-chromium alloys, and zinc-tungsten alloys. In addition, after a stent shape is formed, plating with such a metallic material as above-mentioned may be carried out. Further, after a final stent shape is formed, annealing is preferably carried out. When the stent is annealed, flexibility and plasticity of the stent as a whole are enhanced, and better properties for indwelling in a bent blood vessel can be realized. As compared with the case where annealing is not conducted, the force for restoring the pre-expansion shape that is exhibited after expansion of the stent, particularly the force for returning into a straight shape that is exhibited after the stent is expanded in a bent blood vessel portion, is reduced, so that the physical stimulus given by the stent to the inside wall of the bent blood vessel is reduced, and the cause of restenosis can be reduced. In order to prevent formation of an oxide film on the stent surface, the annealing is preferably carried out by heating the stent at a temperature of 900 to 1200 degrees C. under an inert gas atmosphere (for example, argon gas), followed by slow cooling.

The stent disclosed here is made of such a metal as described above, at least at its portion brought into contact with the balloon. Of the stent, those portions which are not brought into contact with the balloon may not necessarily be made of metal. For instance, a stent entirely made of metal may be adopted. In addition to the metallic stent, a stent with a two-layer structure composed of a metallic layer and a non-metallic layer may be adopted. For example, a stent wherein a metallic stent is coated with a non-metallic layer, and a stent wherein a non-metallic (e.g., polymer-made) stent is plated with metal, may also be adopted. Further, stents with a multilayer (three-layers or more than three layers) structure wherein metallic layer(s) and non-metallic (e.g., polymer-made) layer(s) are alternately laminated may also be adopted. Here, examples of the non-metallic layer include polymer layers, drug coat layers, and surface lubricating layers. That portion of the balloon which is not brought into contact with the balloon is not specifically restricted insofar as it is a stent portion that is not brought into contact with the balloon. Such a portion is preferably a portion near the living body tissue, more preferably a portion put in contact with the living body tissue, and particularly preferably a portion on the side opposite to the portion brought into contact with the balloon. The portion on the side opposite to the portion making contact with the balloon is the closest to the living body tissue, and at least partly comes into direct contact with the living body tissue. At this portion, therefore, an effective component (e.g., a drug or a lubricant) contained in the above-mentioned layer can be directly absorbed through the living body tissue, without flowing in the body fluid such as blood. Accordingly, local administration of the effective component can be realized, whereby more effective physiological activity can be achieved. Among these structures, a structure wherein a drug coat layer is provided on a stent portion on the side opposite to the stent portion making contact with the balloon is particularly preferable.

Here, the drug coat layer may be formed from any material, and is preferably formed from a bioabsorbable material and a drug. This helps ensure that after the stent is put indwelling in a stenosed part, the drug is released over time, attendantly on the in vivo decomposition and absorption of the bioabsorbable material, to exhibit an effect of restraining restenosis or the like, while on the other hand the bioabsorbable material can be completely decomposed in the living body. Here, the thickness of the drug coat layer is not particularly limited. It is preferable, however, that the thickness is set at such a level that stent performances such as deliverability to a lesion part and stimulus to the blood vessel wall will not be spoiled and that the effect of the drug (biologically active agent) can be confirmed. Taking this point into account, the thickness of the drug coat layer is preferably 1 to 100 μm, more preferably 10 to 60 μm.

The method for providing the drug coat layer on a surface of the stent is not specifically restricted. Examples of the method which can be used here include a method in which the drug (biologically active agent) and the bioabsorbable material are melted and used to coat a surface of the stent, a method in which the drug (biologically active substance) and the bioabsorbable material are dissolved in a solvent to prepare a solution, the stent is immersed in the solution and then pulled up, and the solvent is removed by transpiration or the like, and a method in which the above-mentioned solution is sprayed onto the stent by use of a spray and thereafter the solvent is removed by transpiration or the like.

Here, the bioabsorbable material is not specifically restricted so long as it is a polymer which is gradually biodegradable and which does not produce any adverse effect on the living body of a human or animal. It is preferable, however, that the bioabsorbable material is high in biostability. Specific examples of the bioabsorbable material include bioabsorbable aliphatic polyesters such as polylactic acid, polyglycolic acid, lactic acid-glycolic acid copolymer, polycaprolactone, lactic acid-caprolactone copolymer, glycolic acid-caprolactone copolymer, polytrimethylene carbonate, lactic acid-trimethylene carbonate copolymer, glycolic acid-trimethylene carbonate copolymer, polydioxanone, polyethylene succinate, polybutylene succinate, polybutylene succinate adipate, polyhydroxylactic acid, polymalic acid, etc.; at least one polymer selected from the group consisting of polymers of poly-α-amino acid, collagen, laminin, heparan sulfate, fibronectin, vitronectin, chondroitin sulfate, hyaluronic acid, and polymers of cinnamic acid as well as polymers of cinnamic acid derivatives, copolymers formed by arbitrary copolymerization of some of the monomers constituting the above-mentioned polymers, and mixtures of the above-mentioned polymers and/or the above-mentioned copolymers. The "mixtures" herein is used as a wide concept which includes complexes such as polymer alloys and the like. In addition, the weight average molecular weight of the bioabsorbable material is not particularly limited, and is preferably 10,000 to 1,000,000, more preferably 20,000 to 500,000, and particularly preferably 50,000 to 200,000. Measurement of the above-mentioned "weight average molecular weight" can be carried out by a known method such as GPC, light scattering method, viscometry, and mass spectrometry (TOFMASS or the like). The "weight average molecular weight" herein means the value measured by GPC, with polystyrene whose molecular weight has been known as a reference substance. The above-mentioned bioabsorbable materials may be used either singly or in the form of a mixture of two or more of them. Among these, the bioabsorbable aliphatic polyesters, particularly, are advantageous in that they are decomposed and absorbed in vivo with the lapse of time, so that they can avoid the risk of chronic inflammation arising from a mechanical stress imposed on the blood vessel wall. In other words, they can reduce or eliminate invasiveness onto the living body. Among the above-mentioned bioabsorbable aliphatic polyesters, preferred are polylactic acid, polyglycolic acid, lactic acid-glycolic acid copolymer, polycaprolactone, lactic acid-caprolactone copolymer, glycolic acid-caprolactone copolymer, polytrimethylene carbonate, lactic acid-trimethylene carbonate copolymer, glycolic acid-trimethylene carbonate copolymer, polydioxanone, polyethylene succinate, polybutylene succinate, and polybutylene succinate adipate, and more preferred are polylacic acid, polyglycolic acid, lactic acid-glycolic acid copolymer, lactic acid-trimethylene carbonate copolymer, and glycolic acid-trimethylene carbonate copolymer. These are high in safety on a medical basis, even after decomposed in vivo. The above-mentioned bioabsorbable aliphatic polyesters may be used either singly or in the form of a mixture of two or more of them. Among the aliphatic polyesters constituting the above-mentioned bioabsorbable aliphatic polyesters, lactic acid includes optical isomers, every one of which is applicable. Thus, the polylactic acid include all of L-polylactic acid, D-polylactic acid, and D,L-polylactic acid. In addition, in the case where the bioabsorbable aliphatic polyester is a copolymer, the structure of the bioabsorbable aliphatic polyester is not specifically restricted; thus, the copolymer may be any of block copolymer, random copolymer, graft copolymer, and alternating copolymer, in structure. The bioabsorbable aliphatic polyesters may each be a purchased one of commercialized ones or may be synthesized. Where the bioabsorbable aliphatic polyester is synthesized, the method for synthesis is not specifically restricted, and a known method may be applied. For instance, in the case of polylactic acid, a lactic acid of the required structure is selected from among L-lactic acid and D-lactic acid as a raw material, and the raw material is subjected to dehydration polycondensation by the lactide method or the direct polymerization method or the like, whereby polylactic acid can be obtained.

In addition, the weight average molecular weight of the above-mentioned bioabsorbable aliphatic polyester is not particularly limited, insofar as bioabsorbability is exhibited. The weight average molecular weight is preferably 10,000 to 3,000,000, more preferably 20,000 to 2,000,000, and particularly preferably 50,000 to 1,000,000. When the weight average molecular weight is in the above-mentioned range, the bioabsorbable aliphatic polyester exhibits sufficient biodegradability, bioabsorbability, moldability and mechanical strength. Measurement of the "weight average molecular weight" can be carried out by a known method such as GPC, light scattering method, viscometry, and mass spectrometry (TOFMASS or the like). The "weight average molecular weight" herein is the value measured by GPC, with polystyrene whose molecular weight has been known as a reference substance.

The drug (biologically active substance) which can be used in the drug coat layer is not specifically restricted, and can be appropriately selected according to the desired drug effect. It is preferable, however, that the drug has an effect to restrain restenosis when the stent with the drug is put indwelling in a stenosed part in a living body lumen. Specific examples of the drug include carcinostatic agent, immunosuppressor, antibiotic, antirheumatic, antithrombogenic agent, HMG-CoA reductase inhibitor, ACE inhibitor, calcium antagonist, antilipemic agent, integrin inhibitor, antiallergic agent, antioxidant, GPIIbIIIa antagonist, retinoid, flavonoid, carotinoid, lipid improver, DNA synthesis inhibitor, tyrosine kinase inhibitor, antiplatelet agent, blood vessel smooth muscle hyperplasia inhibitor, antiflammatory agent, bio-derived material, interferon, and NO production promoting substance.

The carcinostatic agent is preferably, for example, vincristin, vinblastin, vindesin, irinotecan, pirarubicin, paclitaxel, docetaxel, methotrexate, or the like.

The immunosuppressor is preferably, for example, sirolimus, everolimus, biolimus, tacrolimus, azathioprine, cicrosporin, cyclophosphamide, mycophenolate mofetil, gusperimus, mizoribin, or the like.

The antibiotic is preferably, for example, mitomycin, adriamycin, doxorubicin, actinomycin, daunorubicin, idarubicin, pirarubicin, aclarubicin, epirubicin, peplomycin, zinostatin stimalamer, or the like.

The antirheumatic is preferably, for example, methotrexate, sodium thiomalate, salazosulfapyridine, adalimumab, tocilizumab, infliximab, penicillamine, lobenzarit, or the like.

The antithrombogenic agent is preferably, for example, heparin, aspirin, antithrombin preparation, ticlopidine, hirudin, or the like.

The HMG-CoA reductase inhibitor is preferably, for example, cerivastatin, cerivastatin sodium, atorvastatin, rosuvastatin, pitavastatin, fluvastatin, fluvastatin sodium, simvastatin, lovastatin, pravastatin, or the like.

The ACE inhibitor is preferably, for example, quinapril, perindopril erbumine, trandolapril, cilazapril, temocapril, delapril, enalapril maleate, lisinopril, captopril, or the like.

The calcium antagonist is preferably, for example, nifedipine, nilvadipine, diltiazem, benidipine, nisoldipine, or the like.

The antilipemic agent is preferably, for example, probucol. The integrin inhibitor is preferably, for example, AJM300. The antiallergic agent is preferably, for example, tranilast. The antioxixant is preferably, for example, catechins, anthocyanin, proanthocyanidine, lycopene, n-carotene, or the like; among the catechins, particularly preferred is epigallocatechin gallate. The GPIIbIIIa antagonist is preferably, for example, abciximab.

The retinoid is preferably, for example, all-trans-retinoic acid. The flavonoid is preferably, for example, epigallocatechin, anthocyanin, proanthocyanidin, or the like. The carotinoid is preferably, for example, n-carotene, lycopene, or the like. The lipid improver is preferably, for example, eicosapentanoic acid.

The DNA synthesis inhibitor is preferably, for example, 5-FU. The tyrosine kinase inhibitor is preferably, for example, genistein, tyrphostin, erbstatin, or the like. The antiplatelet agent is preferably, for example, ticlopidine, cilostazol, clopidogrel, or the like. The antiflammatory agent is preferably, for example, steroids such as dexamethasone, and prednisolone.

The bio-derived material is preferably, for example, EGF (epidermal growth factor), VEGF (vascular endothelial growth factor), HGF (hepatocyte growth factor), PDGF (platelet derived growth factor), BFGF (basic fibrolast growth factor), or the like.

The interferon is preferably, for example, interferon-γ1a. The NO production promoting substance is preferably, for example, L-alginine.

The above-mentioned drugs (biologically active agents) may be used either singly or in the form of a mixture of two or more of them. The drug (biologically active agent) preferably contain at least one of the above-mentioned substances, from the viewpoint of assured restraint of restenosis. In addition, whether the drug (biologically active agent) is to be one kind of drug (biologically active agent)

or is to be a combination of two or more different kinds of drugs (biologically active agents), the drug should be appropriately selected according to the individual case. In case the stent includes the above-mentioned drug (biologically active agent), the contained amount of the drug (biologically active agent) is not particularly restricted and should be appropriately selected according to the individual case. The contained (blended) amount of the drug (biologically active agent) is preferably 1 to 80 wt %, more preferably 5 to 60 wt %, based on the total weight of the drug (biologically active agent) and the bioabsorbable material. When the contained amount of the drug (biologically active agent) is in such a range, restenosis can be restrained securely.

In this mode, it is preferable that the drug coat layer coats 1 to 100% of the whole surface area of the stent main body, more preferably 50 to 100% of the whole surface area of the stent main body.

(4) Shaft Body

The material(s) to be used for the outer tube shaft 41 and the inner tube shaft 42 constituting the shaft body 4 is not specifically restricted. Those known materials which are commonly used in stent delivery systems can be similarly used, but those which have a certain degree of flexibility are preferred. Specific examples of the applicable material include thermoplastic resins such as polyolefins such as polyethylene, polypropylene, ethylene-propylene copolymer, ethylene-vinyl acetate copolymer, and their cross-linked products and partially cross-linked products (e.g., cross-linked ethylene-vinyl acetate copolymer), polyvinyl chloride, nylon elastomer, polyurethane; silicone rubbers, and latex rubber. Among these materials, preferred are thermoplastic resins, and more preferred are polyolefins, cross-liked polyolefins, and partially cross-linked polyolefins.

In addition, the sizes of the outer tube shaft 41 and the inner tube shaft 42 are not particularly limited, and sizes equivalent or similar to the known sizes commonly used in stent delivery systems are applicable. Specifically, the outside diameter of the outer tube shaft 41 is preferably 0.6 to 1.5 mm, more preferably 0.8 to 1.1 mm. The inside diameter of the outer tube shaft 41 is preferably 0.5 to 1.4 mm, more preferably 0.7 to 1.0 mm. Similarly, the outside diameter of the inner tube shaft 42 is preferably 0.35 to 1.0 mm, more preferably 0.45 to 0.8 mm. The inside diameter of the inner tube shaft 42 is preferably 0.2 to 0.9 mm, more preferably 0.3 to 0.7 mm.

EXAMPLES

The effect of the disclosure here will be described through the following Examples and Comparative Examples. It is to be noted here, however, that the technical scope of the present invention is not limited to the following Examples. In the following Examples and Comparative Examples, each operation was carried out at room temperature (20 to 25 degrees C.), unless specified otherwise.

Example 1

Nylon 12 (Grilamid L25, produced by EMS-CHEMIE Japan Ltd.) and a nylon elastomer (Grilflex ELG5660, produced by EMS-CHEMIE Japan Ltd.) were extruded by a co-extrusion method (two-kind two-layer blow molding method), to produce a two-layer tube (inner layer: Grilamid L25, outer layer: Grilflex ELG5660) having an outside diameter of 0.95 mm, a middle diameter of 0.90 mm, and an inside diameter of 0.56 mm. Next, the tube was subjected to biaxially orienting blow molding, to produce a balloon having a straight tube section outside diameter of 3.5 mm and a straight tube section length of 10.5 mm. Then, an outer tube shaft having an outside diameter of 0.89 mm and a length of 220 mm and an inner tube shaft having an outside diameter of 0.60 mm and a length of 250 mm (which constitute the shaft body) were attached to the balloon, to obtain a balloon catheter.

Next, the balloon was inflated, DBD electrodes were attached to a plasma irradiation system (DURADYNE PT-2000P, produced by TRI-STAR TECHNOLOGIES), and the balloon was subjected to an argon ionized gas plasma treatment under an atmospheric pressure for 5 seconds under the conditions of a GAS FLOW of 15 SCFH and a PLASMA CURRENT of 0.7 A (plasma treatment before application of thiol compound).

The balloon having undergone the plasma treatment before application of thiol compound was immersed in a 0.7 wt % solution of tris[(3-mercaptopropionyloxy)ethyl] isocyanurate (TEMPIC) (having three thiol groups in one molecule) (produced by SC Organic Chemical Co., Ltd.) in THF, and, after drying, was subjected again to an argon ionized gas plasma treatment under the atmospheric pressure for 5 seconds by use of the above-mentioned plasma irradiation system. Thereafter, the balloon was immersed in a 2.0 wt % solution of TEMPIC in THF, and, after drying, was subjected further to a plasma treatment for 15 seconds by use of the above-mentioned plasma irradiation system (plasma treatment after application of thiol compound). The balloon catheter having undergone the above-mentioned treatments was heated at 55 degrees C. for 12 hours, and a stainless steel (SUS316L) stent (outside diameter=2.0 mm, length=8.0 mm, wall thickness=130 μm) shown in FIG. 3 was mounted thereon, followed by crimping, to obtain a stent delivery system (1) of balloon-expandable stent.

Example 2

A stent delivery system (2) of balloon-expandable stent was obtained in the same manner as in Example 1, except that heating at 55 degrees C. for 12 hours was again conducted after the stent was mounted and crimped.

Comparative Example 1

Nylon 12 (Grilamid L25, produced by EMS-CHEMIE Japan Ltd.) and a nylon elastomer (Griflex ELG5660, produced by EMS-CHEMIE Japan Ltd.) were extruded by a co-extrusion method (two-kind two-layer blow molding method), to produce a two-layer tube (inner layer: Grilamid L25, outer layer: Griflex ELG5660) having an outside diameter of 0.95 mm, a middle diameter of 0.90 mm, and an inside diameter of 0.56 mm. Next, the tube was subjected to biaxially orienting blow molding, to produce a balloon having a straight tube section outside diameter of 3.50 mm and a straight tube section length of 10.5 mm. Then, the same outer tube shaft and inner tube shaft as in Example 1 were attached to the balloon, to obtain a balloon catheter.

The same stainless steel stent as in Example 1 was mounted on the balloon, followed by crimping, to obtain a comparative stent delivery system (1)' of balloon-expandable stent.

Comparative Example 2

A comparative stent delivery system (2)' of balloon-expandable stent was obtained in the same manner as in Comparative Example 1, except that heating at 55 degrees C. for 12 hours was again conducted after the stent was mounted and crimped.

For the stent delivery systems (1) and (2) of balloon-expandable stent and the comparative stent delivery systems (1)' and (2)' of balloon-expandable stent which were respectively obtained in Examples 1 and 2 and Comparative Examples 1 and 2, shifting of the stent from the balloon under load was evaluated as stent shifting strength by the following retention measuring test. The results are set forth in Table 1 below.

Retention Measuring Test

Figure 5A:
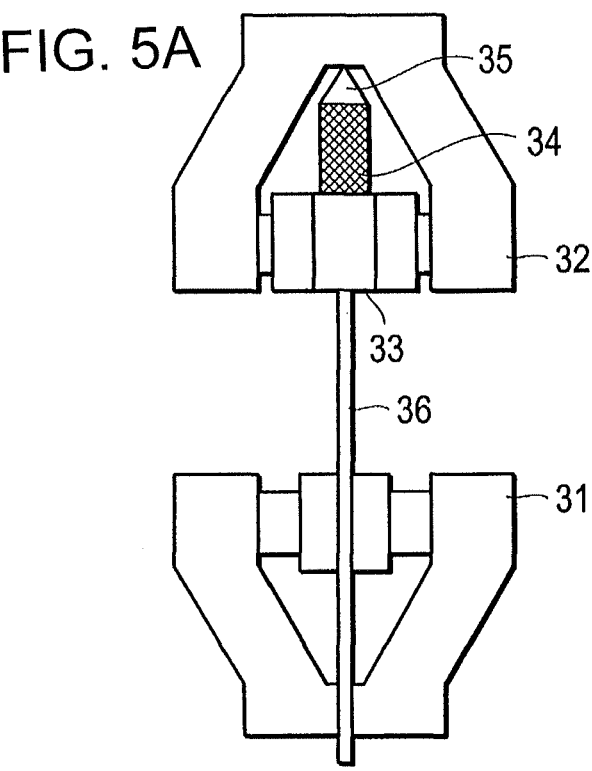
FIG. 5A is a schematic illustration of an instrument used for a retention measuring test.
Figure 5B:
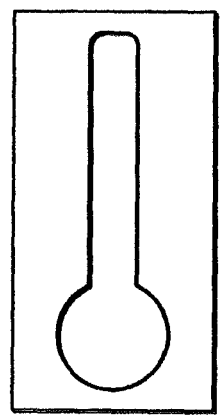
FIG. 5B is a top view of a shifting strength measuring jig 33 shown in FIG. 5A.

In warm water at 37(+/−2) degrees C., a guiding catheter (Launcher 5F AL2.0, produced by Medtronic) was engaged by use of a blood vessel model (ASTM standard: F2394-07), and a guide wire (Runthrough NS 0.014 inch, produced by Terumo Corporation) was inserted into the depth of the blood vessel model through a peripheral end of the blood vessel model. After the guiding catheter and the blood vessel model were substituted with water (i.e., water is poured in the guiding catheter and the blood vessel model so that the catheter and the model are filled with water), each of the stent delivery systems obtained in the Examples and Comparative Examples was set along the guide wire, was then slid three times from the distal end of the guiding catheter to the peripheral end of the blood vessel model, and was thereafter pulled out of the blood vessel model. Next, as shown in FIGS. 5A and 5B, for each stent delivery system with a core metal inserted in a guide wire lumen of the shaft body 36, the shaft body 36 was fixed to a chuck part 31 on the main body side of an autograph (TGE-1kN, produced by Minebea Co., Ltd.). Thereafter, a shifting strength measuring jig 33 was fixed to a chuck part 32 on the load cell side, and a proximal portion of the stent 34 was hooked on the upper end of the jig 33. The jig was pulled upward under the following test conditions, and the maximum value of the load exerted until the stent starts shifting was determined as stent shifting strength (N). In this test, a higher value of the stent shifting strength (N) means that the stent is less liable to drop off or shift from the balloon.

Test Conditions

Load cell used: 50 N
Pulling-upward speed: 200 mm/minute
Core metal: 0.39 mm in diameter

TABLE 1

Results of retention measuring test

| Test conditions | Stent shifting strength (N) |
|---|---|
| Example 1: Coated, Not heated | 1.000 |
| Example 2: Coated, Heated after stent crimping | 1.320 |
| Comparative Example 1: Not coated, Not heated | 0.581 |
| Comparative Example 2: Not coated, Heated after stent crimping | 0.435 |

As is clear from the results set forth in Table 1, the stent delivery systems (1) and (2) of balloon-expandable stent which were obtained in Examples 1 and 2 gave significantly higher values of stent shifting strength, as compared with the comparative stent delivery systems (1)' and (2)' of balloon-expandable stent which were obtained in Comparative Examples 1 and 2. Thus, it is considered that the stent delivery system according to the disclosure here can sufficiently endure the strong load due to friction at the time of insertion into a stenosed part in a living body lumen, and can effectively restrain or prevent the stent from dropping off from, or shifting on, the balloon.

Example 3

Nylon 12 (Grilamid L25, produced by EMS-CHEMIE Japan Ltd.) and a nylon elastomer (Grilflex ELG5660, produced by EMS-CHEMIE Japan Ltd.) were extruded by a co-extrusion method (two-kind two-layer blow molding method), to produce a two-layer tube (inner layer: Grilamid L25, outer layer: Grilflex ELG5660) having an outside diameter of 0.95 mm, a middle diameter of 0.90 mm, and an inside diameter of 0.56 mm. Next, the tube was subjected to biaxially orienting blow molding, to produce a balloon having a straight tube section outside diameter of 3.5 mm and a straight tube section length of 10.5 mm. Then, an outer tube shaft having an outside diameter of 0.89 mm and a length of 220 mm and an inner tube shaft having an outside diameter of 0.56 mm and a length of 250 mm (which constitute the shaft body) were attached to the balloon, to obtain a balloon catheter.

Next, the balloon was inflated, DBD electrodes were attached to a plasma irradiation system (DURADYNE PT-2000P, produced by TRI-STAR TECHNOLOGIES), and the balloon was subjected to an argon ionized gas plasma treatment under an atmospheric pressure for 15 seconds under the conditions of a GAS FLOW of 15 SCFH and a PLASMA CURRENT of 0.7 A (plasma treatment before application of thiol compound).

The balloon having undergone the plasma treatment before application of thiol compound was immersed in a 5.0 wt % solution of tris[(3-mercaptopropionyloxy)ethyl] isocyanurate (TEMPIC) (having three thiol groups in one molecule) (produced by SC Organic Chemical Co., Ltd.) in THF, and, after drying, was subjected again to an argon ionized gas plasma treatment under the atmospheric pressure for 15 seconds by use of the above-mentioned plasma irradiation system (plasma treatment after application of thiol compound). The balloon catheter having undergone the above-mentioned treatment was heated at 60 degrees C. for 12 hours, and a stainless steel (SUS316L) stent (outside diameter=2.0 mm, length=8.5 mm, wall thickness=130 μm) shown in FIG. 3 was mounted thereon, followed by crimping. Thereafter, the balloon catheter was subjected again to a heating treatment at 60 degrees C. for 12 hours, to obtain a stent delivery system (3) of balloon-expandable stent.

Example 4

A stent delivery system (4) of balloon-expandable stent was obtained by the same method as in Example 3, except that a solution containing 5.0 wt % of TEMPIC and 0.5 wt % of pentaerythritol tetrakis(3-mercaptopropionate) (PEMP) (having four thiol groups in one molecule) (produced by SC Organic Chemical Co., Ltd.) in THF was used in place of the 5.0 wt % solution of TEMPIC in THF which was used in Example 3.

Example 5

A stent delivery system (5) of balloon-expandable stent was obtained by the same method as in Example 3, except that a solution containing 5.0 wt % of TEMPIC and 0.25 wt % of 2,2-dimethoxy-2-phenylacetophenone (produced by Tokyo Chemical Industry Co., Ltd.) in THF was used in place of the 5.0 wt % solution of TEMPIC in THF which was used in Example 3.

Example 6

A balloon produced by the same method as in Example 3 was immersed in a 50 wt % solution of butylated hydroxyanisole (BHA) in methanol for 3 minutes. Next, the balloon was immersed in a 5.0 wt % solution of TEMPIC in THF, and, after drying, was subjected to irradiation with an argon ionized gas plasma under an atmospheric pressure for 30 seconds by use of the same plasma irradiation system as in Example 3 (plasma treatment after application of thiol compound). The balloon catheter having undergone the above-mentioned treatment was heated at 60 degrees C. for 12 hours, and a stainless steel (SUS316L) stent (outside diameter=2.0 mm, length=8.5 mm, wall thickness=130 μm) shown in FIG. 3 was mounted thereon, and crimped. Thereafter, the balloon catheter was again subjected to a heating treatment at 60 degrees C. for 12 hours, to obtain a stent delivery system (6) of balloon-expandable stent.

For the stent delivery systems (3) to (6) obtained in Examples 3 to 6 as above, the shifting of the stent from the balloon under load was evaluated as stent shifting strength by the same method as that described in Example 1. The results are set forth in Table 2 below.

TABLE 2

Results of retention measuring test

| Test conditions | Stent shifting strength (N) |
| --- | --- |
| Example 3: 5.0 wt % TEMPIC | 1.01 |
| Example 4: 5.0 wt % TEMPIC + 0.5 wt % PEMP | 4.10 |
| Example 5: 5.0 wt % TEMPIC + 0.25 wt % Photoinitiator | 4.61 |
| Example 6: After BHA treatment, 5.0 wt % TEMPIC | 3.52 |

As is clear from the results set forth in Table 2, the stent delivery systems (3) to (6) of balloon-expandable stent which were obtained in Examples 3 to 6 gave sufficiently high values of stent shifting strength. Thus, it is considered that the stent delivery system according to the disclosure here can sufficiently endure the strong load due to friction at the time of insertion into a stenosed part in a living body lumen, and can efficiently restrain or prevent the stent from dropping off from, or shifting on, the balloon.

Example 7

Nylon 12 (Grilamid L25, produced by EMS-CHEMIE Japan Ltd.) and a nylon elastomer (Grilflex ELG5660, produced by EMS-CHEMIE Japan Ltd.) were extruded by a co-extrusion method (two-kind two-layer blow molding method), to produce a two-layer tube (inner layer: Grilamid L25, outer layer: Grilflex ELG5660) having an outside diameter of 0.95 mm, a middle diameter of 0.90 mm, and an inside diameter of 0.56 mm. Next, the tube was subjected to biaxially orienting blow molding, to produce a balloon having a straight tube section outside diameter of 3.5 mm and a straight tube section length of 11.8 mm. Then, an outer tube shaft having an outside diameter of 0.89 mm and a length of 220 mm and an inner tube shaft having an outside diameter of 0.56 mm and a length of 250 mm (which constitute the shaft body) were attached to the balloon, to obtain a balloon catheter.

Next, the balloon was inflated, DBD electrodes were attached to a plasma irradiation system (DURADYNE PT-2000P, produced by TRI-STAR TECHNOLOGIES), and the balloon was subjected to an argon ionized gas plasma treatment under an atmospheric pressure for 15 seconds under the conditions of a GAS FLOW of 15 SCFH and a PLASMA CURRENT of 0.7 A (plasma treatment before application of thiol compound).

The balloon having undergone the plasma treatment before application of thiol compound was immersed in a 5.0 wt % solution of tris[(3-mercaptopropionyloxy)ethyl]isocyanurate (TEMPIC) (having three thiol groups in one molecule) (produced by SC Organic Chemical Co., Ltd.) in THF, and, after drying, was subjected again to an argon ionized gas plasma treatment under the atmospheric pressure for 15 seconds by use of the above-mentioned plasma irradiation system (plasma treatment after application of thiol compound). The balloon catheter having undergone the above-mentioned treatment was heated at 60 degrees C. for 12 hours, and a CoCr alloy (L605) stent (outside diameter=2.0 mm, length=8.9 mm, wall thickness=80 μm) shown in FIG. 3 was mounted thereon, followed by crimping. Thereafter, the balloon catheter was subjected again to a heating treatment at 60 degrees C. for 12 hours, to obtain a stent delivery system (7) of balloon-expandable stent.

Example 8

A stent delivery system (8) of balloon-expandable stent was obtained by the same method as in Example 7, except that a solution containing 5.0 wt % of TEMPIC and 0.5 wt % of pentaerythritol tetrakis(3-mercaptopropionate) (PEMP) (having four thiol groups in one molecule) (produced by SC Organic Chemical Co., Ltd.) in THF was used in place of the 5.0 wt % solution of TEMP IC in THF which was used in Example 7.

Example 9

A stent delivery system (9) of balloon-expandable stent was obtained by the same method as in Example 7, except that a solution containing 0.5 wt % of TEMPIC and 5.0 wt % of pentaerythritol tetrakis(3-mercaptopropionate) (PEMP) (having four thiol groups in one molecule) (produced by SC Organic Chemical Co., Ltd.) in THF was used in place of the 5.0 wt % solution of TEMP IC in THF which was used in Example 7.

Example 10

A balloon produced by the same method as in Example 7 was immersed in a 50 wt % solution of butylated hydroxyanisole (BHA) in methanol for 3 minutes. Next, the balloon was immersed in a 5.0 wt % solution of TEMPIC in THF, and, after drying, was subjected to irradiation with an argon ionized gas plasma under an atmospheric pressure for 30 seconds by use of the same plasma irradiation system as in Example 7 (plasma treatment after application of thiol compound). The balloon catheter having undergone the above-mentioned treatment was heated at 60 degrees C. for 12 hours, and a Co—Cr alloy (L605) stent (outside diameter=2.0 mm, length=8.9 mm, wall thickness=80 μm) shown in FIG. 3 was mounted thereon, and crimped. Thereafter, the balloon catheter was again subjected to a heating treatment at 60 degrees C. for 12 hours, to obtain a stent delivery system (10) of balloon-expandable stent.

Comparative Example 3

Nylon 12 (Grilamid L25, produced by EMS-CHEMIE Japan Ltd.) and a nylon elastomer (Grilflex ELG5660, produced by EMS-CHEMIE Japan Ltd.) were extruded by a co-extrusion method (two-kind two-layer blow molding method), to produce a two-layer tube (inner layer: Grilamid L25, outer layer: Grilflex ELG5660) having an outside diameter of 0.95 mm, a middle diameter of 0.90 mm, and an inside diameter of 0.56 mm. Next, the tube was subjected to biaxially orienting blow molding, to produce a balloon having a straight tube section outside diameter of 3.5 mm and a straight tube section length of 11.8 mm. Then, an outer tube shaft having an outside diameter of 0.89 mm and a length of 220 mm and an inner tube shaft having an outside diameter of 0.56 mm and a length of 250 mm (which constitute the shaft body) were attached to the balloon, to obtain a balloon catheter. A CoCr alloy (L605) stent (outside diameter=2.0 mm, length=8.9 mm, wall thickness=80 μm) was mounted on the balloon, followed by crimping. Thereafter, the balloon catheter was subjected to a heating treatment at 60 degrees C. for 12 hours, to obtain a comparative stent delivery system (3)' of balloon-expandable stent.

For the stent delivery systems (7) to (10) of balloon-expandable stent which were obtained in Examples 7 to 10 above and the comparative stent delivery systems (3)' of balloon-expandable stent which was obtained in Comparative Example 3, the shifting of the stent from the balloon under load was evaluated as stent shifting strength by the same method as that described in Example 1. The results are set forth in Table 3 below.

TABLE 3

Results of retention measuring test

| Test conditions | Stent shifting strength (N) |
| --- | --- |
| Example 7: 5.0 wt % TEMPIC | 1.37 |
| Example 8: 5.0 wt % TEMPIC + 0.5 wt % PEMP | 3.41 |
| Example 9: 0.5 wt % TEMPIC + 5.0 wt % PEMP | 2.58 |
| Example 10: After BHA treatment, 5.0 wt % TEMPIC | 2.83 |
| Comparative Example 3: Untreated | 0.82 |

As is clear from the results set forth in Table 3, the stent delivery systems (7) to (10) of balloon-expandable stent which were obtained in Examples 7 to 10 gave significantly higher values of stent shifting strength, as compared with the comparative stent delivery system (3)' of balloon-expandable stent which was obtained in Comparative Example 3. Thus, it is considered that the stent delivery system according to the disclosure here can sufficiently endure the strong load due to friction at the time of insertion into a stenosed part in a living body lumen, and can restrain or prevent the stent from dropping off from, or shifting on, the balloon.

The detailed description above describes a stent delivery system disclosed by way of example. The invention is not limited, however, to the precise embodiment and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent delivery system comprising:
an inner tube positioned inside an outer tube, the outer tube possessing a distal end and an inner surface, the inner tube possessing an outer surface and a distal end extending distally beyond the distal end of the outer tube, and a balloon inflation lumen located between the inner surface of the outer tube and the outer surface of the inner tube;
a balloon possessing a distal end fixed to a distal end portion of the inner tube and a proximal end fixed to the distal end of the outer tube, the balloon possessing an outer surface and an interior communicating with the balloon inflation lumen located between the inner surface of the outer tube and the outer surface of the inner tube;
a hollow cylindrically shaped stent possessing open opposite ends, the stent possessing an inner surface and an outer surface that communicate with one another by way of a plurality of cutouts provided in the hollow cylindrically shaped stent, the stent being expandable and contractable in a radial direction of the hollow cylindrically shaped stent, at least a part of the stent being made of metal, the balloon being positioned inside the hollow cylindrically shaped stent so that the hollow cylindrically shaped stent encircles the balloon;
a layer positioned between the outer surface of the balloon and the hollow cylindrically shaped stent, at least a portion of the metal part of the hollow cylindrically shaped stent being bonded to the layer, the layer being formed from at least one compound with a plurality of thiol groups in its molecule, and the outer surface of the balloon supporting the at least one compound with the plurality of thiol groups, and
wherein manufacturing the stent delivery system comprises applying the balloon to plasma treatment, followed by subjecting the balloon to heat treatment and followed by applying the layer to modify or activate the outer surface of the balloon to effect a bonding reaction between the at least one compound with a plurality of thiol groups and the outer surface of the balloon.

2. The stent delivery system according to claim 1, wherein the layer positioned between the outer surface of the balloon and the hollow cylindrically shaped stent covers only a part of the outer surface of the balloon.

3. The stent delivery system according to claim 1, wherein the compound with the thiol groups is at least one selected from the group consisting of 1,2-ethanedithiol, 1,2-propanedithiol, 1,3-propanedithiol, 1,4-butanedithiol, 2,3-butanedithiol, 1,5-pentanedithiol, 1,6-hexanedithiol, 1,8-octanedithiol, 3,6-dioxa-1,8-octanedithiol, bis(2-mercaptoethyl) ether, bis(2-mercaptoethyl) sulfide, 1,2-benzenedithiol, 1,4-benzenedithiol, 1,4-bis(mercaptomethyl)benzene, toluene-3,4-dithiol, 1,5-dimercaptonaphthalene, 4,4'-biphenyldithiol, 4,4'-thiobisbenzenethiol, tetraethylene glycol bis(3-mercaptopropionate), 1,3,5-benzenetrithiol, tris[(3-mercaptopropionyloxy)ethyl] isocyanurate, triazinetrithiol, trimethylolpropane tris(3-mercaptopropionate), pentaerythritol tetrakis (mercaptoacetate), pentaerythritol tetrakis(3-mercaptopropionate), pentaerythritol tetrakis(3- mercaptobutyrate), dipentaerythritol hexakis(3-mercaptopropionate), and their derivatives and polymers.

4. The stent delivery system according to claim 1, wherein the metal part of the hollow cylindrically shaped stent bonded to the layer is on one side of the stent, the stent possessing an opposite side that is opposite the one side, and further comprising a drug coat layer on at least the opposite side of the stent.

5. The stent delivery system according to claim 1, wherein manufacturing the stent delivery system comprises adding a photoinitiator to the at least one compound with a plurality of thiol groups before applying the balloon to plasma treatment.

6. The stent delivery system according to claim 1, wherein manufacturing the stent delivery system comprises immersing the balloon in a solution comprising butylated hydroxyanisole before applying the balloon to plasma treatment.

7. The stent delivery system according to claim 1, the at least one compound with a plurality of thiol groups includes at least one compound with 2 thiol groups in its molecule and at least one compound with 3 thiol groups in its molecule.

8. The stent delivery system according to claim 1, the at least one compound with a plurality of thiol groups includes at least one compound with 2 thiol groups in its molecule and at least one compound with 4 thiol groups in its molecule.

9. The stent delivery system according to claim 1, the at least one compound with a plurality of thiol groups includes at least one compound with 3 thiol groups in its molecule and at least one compound with 4 thiol groups in its molecule.

10. A stent delivery system comprising:
a tube-shaped shaft body;
a balloon provided at a distal portion of the shaft body, the balloon possessing an outer surface;
a stent drop-off preventing layer on at least a portion of the outer surface of the balloon to prevent drop-off of the stent from the balloon, the stent drop-off preventing layer being formed from a compound with a plurality of thiol groups in its molecule;
a stent encircling the balloon and contacting the stent drop-off preventing layer;
at least a portion of the stent which makes contact with the stent drop-off preventing layer being made of a metal, and
wherein the compound with the thiol groups is at least one selected from the group consisting of 1,2-ethanedithiol, 1,2-propanedithiol, 1,3-propanedithiol, 1,4-butanedithiol, 2,3-butanedithiol, 1,5-pentanedithiol, 1,6-hexanedithiol, 1,8-octanedithiol, 3,6-dioxa-1,8-octanedithiol, bis(2-mercaptoethyl) ether, bis(2-mercaptoethyl) sulfide, 1,2-benzenedithiol, 1,4-benzenedithiol, 1,4-bis(mercaptomethyl)benzene, toluene-3,4-dithiol, 1,5-dimercaptonaphthalene, 4,4'-biphenyldithiol, 4,4'-thiobisbenzenethiol, tetraethylene glycol bis(3-mercaptopropionate), 1,3,5-benzenetrithiol, tris[(3-mercaptopropionyloxy)ethyl]isocyanurate, triazinetrithiol, trimethylolpropane tris(3-mercaptopropionate), pentaerythritol tetrakis(mercaptoacetate), pentaerythritol tetrakis(3-mercaptopropionate), pentaerythritol tetrakis(3-mercaptobutyrate), dipentaerythritol hexakis(3-mercaptopropionate), and their derivatives and polymers.

11. The stent delivery system according to claim 10, wherein the compound with the thiol groups is supported on the outer surface of the balloon by irradiation with an ionized gas plasma.

12. The stent delivery system according to claim 11, wherein the portion of the stent making contact with the stent drop-off preventing layer is on one side of the stent, and the stent including an other side opposite the one side, and further comprising a drug coat layer on at least a portion of the stent that is on the other side of the stent.

13. The stent delivery system according to claim 10, wherein the portion of the stent making contact with the stent drop-off preventing layer is on one side of the stent, and the stent including an other side opposite the one side, and further comprising a drug coat layer on at least a portion of the stent that is on the other side of the stent.

14. A stent delivery system comprising:
an inner tube positioned inside an outer tube, the outer tube possessing a distal end and an inner surface, the inner tube possessing an outer surface and a distal end extending distally beyond the distal end of the outer tube, and a balloon inflation lumen located between the inner surface of the outer tube and the outer surface of the inner tube;
a balloon possessing a distal end fixed to a distal end portion of the inner tube and a proximal end fixed to the distal end of the outer tube, the balloon possessing an outer surface and an interior communicating with the balloon inflation lumen located between the inner surface of the outer tube and the outer surface of the inner tube;
a hollow cylindrically shaped stent possessing open opposite ends, the stent possessing an inner surface and an outer surface that communicate with one another by way of a plurality of cutouts provided in the hollow cylindrically shaped stent, the stent being expandable and contractable in a radial direction of the hollow cylindrically shaped stent, at least a part of the stent being made of metal, the balloon being positioned inside the hollow cylindrically shaped stent so that the hollow cylindrically shaped stent encircles the balloon;
a layer positioned between the outer surface of the balloon and the hollow cylindrically shaped stent, at least a portion of the metal part of the hollow cylindrically shaped stent being bonded to the layer, the layer being formed from at least one compound with a plurality of thiol groups in its molecule, and the outer surface of the balloon supporting the at least one compound with the plurality of thiol groups, and
wherein manufacturing the stent delivery system comprises subjecting the outer surface of the balloon to plasma treatment followed by applying the layer to modify or activate the outer surface of the balloon to effect a bonding reaction between the at least one compound with a plurality of thiol groups and the outer surface of the balloon, and subjecting the balloon to plasma treatment following the application of the layer.

15. The stent delivery system according to claim 14, wherein manufacturing the stent delivery system further comprises subjecting the balloon to heat treatment after subjecting the balloon to plasma treatment following the application of the layer.

\* \* \* \* \*